United States Patent
Salaita et al.

(10) Patent No.: US 11,136,595 B2
(45) Date of Patent: Oct. 5, 2021

(54) PARTICLES COATED WITH CATALYSTS USEFUL FOR SPLICING NUCLEIC ACIDS

(71) Applicant: Emory University, Atlanta, GA (US)

(72) Inventors: Khalid Salaita, Decatur, GA (US); Jessica Petree, Lawrenceville, GA (US); Kevin Yehl, Quincy, MA (US)

(73) Assignee: Emory University, Atlanta, GA (US)

( * ) Notice: Subject to any disclaimer, the term of this patent is extended or adjusted under 35 U.S.C. 154(b) by 98 days.

(21) Appl. No.: 16/180,786

(22) Filed: Nov. 5, 2018

(65) Prior Publication Data

US 2019/0136264 A1 May 9, 2019

Related U.S. Application Data

(60) Provisional application No. 62/581,422, filed on Nov. 3, 2017.

(51) Int. Cl.

| | |
|---|---|
| *C12N 15/52* | (2006.01) |
| *C12N 15/90* | (2006.01) |
| *C12Q 1/6823* | (2018.01) |
| *C12N 9/00* | (2006.01) |
| *C12N 9/22* | (2006.01) |
| *C12N 15/10* | (2006.01) |
| *C12N 15/113* | (2010.01) |
| *B82Y 5/00* | (2011.01) |

(52) U.S. Cl.
CPC ............ *C12N 15/902* (2013.01); *C12N 9/22* (2013.01); *C12N 9/93* (2013.01); *C12N 15/102* (2013.01); *C12N 15/113* (2013.01); *C12N 15/52* (2013.01); *C12Q 1/6823* (2013.01); *C12Y 605/01004* (2013.01); *B82Y 5/00* (2013.01); *C12N 2310/127* (2013.01); *C12N 2320/33* (2013.01); *C12Y 301/00* (2013.01)

(58) Field of Classification Search
CPC .... C12N 15/902; C12N 15/113; C12N 15/52; C12N 9/93; C12N 9/22; C12N 15/102; C12N 2310/127; C12N 2320/33; C12Q 1/6823; C12Y 605/01004; C12Y 301/00; B82Y 5/00
See application file for complete search history.

(56) References Cited

U.S. PATENT DOCUMENTS

| 7,569,340 | B2 | 8/2009 | Mirkin | |
|---|---|---|---|---|
| 8,220,317 | B2 | 7/2012 | Mirkin | |
| 8,962,238 | B2 * | 2/2015 | Todd | C12Q 1/6811 435/6.1 |
| 9,545,421 | B2 | 1/2017 | Nelson | |
| 9,605,304 | B2 | 3/2017 | Lee | |
| 9,708,665 | B2 | 7/2017 | Salaita | |
| 9,803,197 | B2 | 10/2017 | Yehl | |
| 10,155,946 | B2 | 12/2018 | Yehl | |
| 2017/0114400 | A1 | 4/2017 | Salaita | |
| 2017/0260575 | A1 | 9/2017 | Salaita | |

FOREIGN PATENT DOCUMENTS

WO 2004081235 9/2004

OTHER PUBLICATIONS

Of Liu et al. (Analytical Methods 2017, vol. 9, pp. 2633-2643). (Year: 2017).*
Baum et al. Deoxyribozymes: useful DNA catalysts in vitro and in vivo, Cell. Mol. Life Sci. 65 (2008) 2156-2174.
Chakravarty et al. RNA ligase RtcB splices 3'-phosphate and 5'-OH ends via covalent RtcB-(histidinyl)-GMP and polynucleotide-(3')pp(5')G intermediates, Proc Natl Acad Sci U S A. 2012,109(16):6072-7.
Das et al. Rewriting the rules for end joining via enzymatic splicing of DNA 3'-PO4 and 5'-OH ends, Proc Natl Acad Sci U S A. 2013,110(51):20437-42.
Desai et al. tRNA Ligase Catalyzes the GTP-Dependent Ligation of RNA with 3'-Phosphate and 5'-Hydroxyl Termini, Biochemistry. 2012, 51(7): 1333-1335.
Englert et al. Structural and mechanistic insights into guanylylation of RNA-splicing ligase RtcB joining RNA between 3'-terminal phosphate and 5'-OH, Proc Natl Acad Sci U S A. 2012, 109(38):15235-40.
Giljohann et al. Gene Regulation with Polyvalent siRNA-Nanoparticle Conjugates, J Am Chem Soc, 2009, 131, 2072-2073.
Haapaniemi et al. CRISPR-Cas9 genome editing induces a p53-mediated DNA damage response, Nat Med. 2018, 24(7):927-930.
Liu et al. Optimization of a Pb2+-Directed Gold Nanoparticle/ DNAzyme Assembly and Its Application as a Colorimetric Biosensor for Pb2+, Chem Mater, 2004, 16, 3231-3238.
Maughan et al. Distinct Contributions of Enzymic Functional Groups to the 2',3'-Cyclic Phosphodiesterase, 3'-Phosphate Guanylylation, and 3'-ppG/5'-OH Ligation Steps of the *Escherichia coli* RtcB Nucleic Acid Splicing Pathway, J Bacteriol, 2016, 198:1294-1304.
Montiel-Gonzales et al. Correction of mutations within the cystic fibrosis transmembrane conductance regulator by site-directed RNA editing, Proc Natl Acad Sci U S A. 2013,110(45):18285-90.
Petree et al. Site-Selective RNA Splicing Nanozyme: DNAzyme and RtcB Conjugates on a Gold Nanoparticle, ACS Chem Biol, 2018, 13, 215-224.
Rosi et al. Oligonucleotide-Modified Gold Nanoparticles for Intracellular Gene Regulation, Science, 2006, 312(5776):1027-30.
Scotti et al. RNA mis-splicing in disease, Nat Rev Genet, 2016, 17(1):19-32.

(Continued)

*Primary Examiner* — J. E. Angell
(74) *Attorney, Agent, or Firm* — Emory Patent Group

(57) ABSTRACT

This disclosure relates to compositions comprising particles conjugated to one or more catalytically cleaving nucleic acids and optionally an RNA ligating enzyme. In certain embodiments, particles reported herein are used for splicing nucleic acid sequences.

16 Claims, 11 Drawing Sheets

Specification includes a Sequence Listing.

(56) References Cited

OTHER PUBLICATIONS

Somasuntharam et al. Knockdown of TNF-α by DNAzyme Gold Nanoparticles as an Anti-inflammatory Therapy for Myocardial Infarction, Biomaterials, 2016, 83:12-22.
Tanaka et al. RtcB Is the RNA Ligase Component of an *Escherichia coli* RNA Repair Operon, J Biol Chem. 2011, 286(10):727-31.
Yang et al. A novel electrochemical DNAzyme sensor for the amplified detection of Pb2+ ions, Chem Commun, 2010, 46, 3107-3109.
Yehl et al. Catalytic Deoxyribozyme-Modified Nanoparticles for RNAi-Independent Gene Regulation, ACS Nano. 2012, 6(10):9150-7.

* cited by examiner

| Construct | Strand Designation | Sequence (5'-3') |
|---|---|---|
| 3 | substrate | FAM/AGACGAGTCTCACGrCrArArGrArArCrArCrGrUrArGrArArCrArGrCrArGrGrrGrUrGrGrArGrArGrCrAGTCGTGAGACTCGTC  SEQ ID NO: 9 |
| 4 | 5' cleaved | FAM/AGACGAGTCTCACGrCrArArGrArArCrArCrG>P  SEQ ID NO: 10 |
| 4 | 3' cleaved | rUrGrGrArGrArGrCrAGTCGTGAGACTCGTC  SEQ ID NO: 11 |
| 5 | spliced | FAM/AGACGAGTCTCACGrCrArArGrArArCrArCrGrUrGrGrArGrArGrCrAGTCGTGAGACTCGTC  SEQ ID NO: 12 |

FIG. 1E

| Construct | Strand Designation | Sequence (5'-3') |
|---|---|---|
| 6 | cDNA | TGGCTCCGATATCACGCTTACTGCTCTCCACCCTGCACCTGGTTTCTCTACGTGTTCTTGCGTGATATCGGAGCCAGATCAGTCGATACATCAGGTATAGTGAGTCGTATTAA  SEQ ID NO: 13 |
| 6 | substrate | FAM/rCrCrUrGrArUrGrUrArUrCrGrArCrUrGrArUrCrUrGrGrCrUrCrCrGrArrUrArUrCrArCrGrCrArArGrArArCrArCrGrUrGrGrArGrArArGrCrArGrGrrUrGrCrArGrGrGrUrGrGrArGrArGrCrArGrUrArArGrCrGrUrGrArUrArUrCrGrGrArGrCrCrA  SEQ ID NO: 14 |
| 7 | 5', cleaved | FAM/rCrCrUrGrArUrGrUrArUrCrGrArCrUrGrArUrCrUrGrGrCrUrCrCrGrArrUrArUrCrArCrGrCrArArGrArArCrArCrGrG>P  SEQ ID NO: 15 |
| 7 | 3', cleaved | rUrGrGrArGrArGrCrArGrUrArArGrCrGrUrGrArUrArUrCrGrGrArGrCrCrA  SEQ ID NO: 16 |
| 8 | spliced | FAM/rCrCrUrGrArUrGrUrArUrCrGrArCrUrGrArUrCrUrGrGrCrUrCrCrGrArrUrArUrCrArCrGrCrArArGrArArCrArCrGrUrGrGrArGrArArGrCrArGrUrArArGrCrGrUrGrArUrArUrCrGrGrArGrCrCrA  SEQ ID NO: 17 |

FIG. 1F

SEQUENCE LISTING

<160> NUMBER OF SEQ ID NOS: 28

<210> SEQ ID NO 1
<211> LENGTH: 410
<212> TYPE: PRT
<213> ORGANISM: Artificial
<220> FEATURE:
<223> OTHER INFORMATION: Synthetic construct

<400> SEQUENCE: 1

Cys Cys Gly Asn Tyr Glu Leu Leu Thr Thr Glu Asn Ala Pro Val Lys

```
1               5                   10                  15
Met Trp Thr Lys Gly Val Pro Val Glu Ala Asp Ala Arg Gln Gln Leu
            20                  25                  30
Ile Asn Thr Ala Lys Met Pro Phe Ile Phe Lys His Ile Ala Val Met
            35                  40                  45
Pro Asp Val His Leu Gly Lys Gly Ser Thr Ile Gly Ser Val Ile Pro
50                  55                  60
Thr Lys Gly Ala Ile Ile Pro Ala Ala Val Gly Val Asp Ile Gly Cys
65                  70                  75                  80
Gly Met Asn Ala Leu Arg Thr Ala Leu Thr Ala Glu Asp Leu Pro Glu
                85                  90                  95
Asn Leu Ala Glu Leu Arg Gln Ala Ile Glu Thr Ala Val Pro His Gly
            100                 105                 110
Arg Thr Gly Arg Cys Lys Arg Asp Lys Gly Ala Trp Glu Asn Pro
            115                 120                 125
Pro Val Asn Val Asp Ala Lys Trp Ala Glu Leu Glu Ala Gly Tyr Gln
            130                 135                 140
Trp Leu Thr Gln Lys Tyr Pro Arg Phe Leu Asn Thr Asn Asn Tyr Lys
145                 150                 155                 160
His Leu Gly Thr Leu Gly Thr Gly Asn His Phe Ile Glu Ile Cys Leu
                165                 170                 175
Asp Glu Ser Asp Gln Val Trp Ile Met Leu His Ser Gly Ser Arg Gly
            180                 185                 190
Ile Gly Asn Ala Ile Gly Thr Tyr Phe Ile Asp Leu Ala Gln Lys Glu
            195                 200                 205
Met Gln Glu Thr Leu Glu Thr Leu Pro Ser Arg Asp Leu Ala Tyr Phe
            210                 215                 220
Met Glu Gly Thr Glu Tyr Phe Asp Asp Tyr Leu Lys Ala Val Ala Trp
225                 230                 235                 240
Ala Gln Leu Phe Ala Ser Leu Asn Arg Asp Ala Met Met Glu Asn Val
                245                 250                 255
Val Thr Ala Leu Gln Ser Ile Thr Gln Lys Thr Val Arg Gln Pro Gln
            260                 265                 270
Thr Leu Ala Met Glu Glu Ile Asn Cys His His Asn Tyr Val Gln Lys
            275                 280                 285
Glu Gln His Phe Gly Glu Glu Ile Tyr Val Thr Arg Lys Gly Ala Val
            290                 295                 300
Ser Ala Arg Ala Gly Gln Tyr Gly Ile Ile Pro Gly Ser Met Gly Ala
305                 310                 315                 320
Lys Ser Phe Ile Val Arg Gly Leu Gly Asn Glu Glu Ser Phe Cys Ser
                325                 330                 335
Cys Ser His Gly Ala Gly Arg Val Met Ser Arg Thr Lys Ala Lys Lys
                340                 345                 350
Leu Phe Ser Val Glu Asp Gln Ile Arg Ala Thr Ala His Val Glu Cys
            355                 360                 365
Arg Lys Asp Ala Glu Val Ile Asp Glu Ile Pro Met Ala Tyr Lys Asp
            370                 375                 380
Ile Asp Ala Val Met Ala Ala Gln Ser Asp Leu Val Glu Val Ile Tyr
385                 390                 395                 400
Thr Leu Arg Gln Val Val Cys Val Lys Gly
                405                 410

<210> SEQ ID NO 2
```

```
<211> LENGTH: 15
<212> TYPE: DNA
<213> ORGANISM: Artificial
<220> FEATURE:
<223> OTHER INFORMATION: Synthetic construct

<400> SEQUENCE: 2
ggctagctac aacga                                                      15

<210> SEQ ID NO 3
<211> LENGTH: 9
<212> TYPE: DNA
<213> ORGANISM: Artificial
<220> FEATURE:
<223> OTHER INFORMATION: Synthetic construct

<400> SEQUENCE: 3 caagaacac                                                              9

<210> SEQ ID NO 4
<211> LENGTH: 9
<212> TYPE: DNA
<213> ORGANISM: Artificial
<220> FEATURE:
<223> OTHER INFORMATION: Synthetic construct

<400> SEQUENCE: 4 uggagagca                                                              9

<210> SEQ ID NO 5
<211> LENGTH: 18
<212> TYPE: DNA
<213> ORGANISM: Artificial
<220> FEATURE:
<223> OTHER INFORMATION: Synthetic construct

<400> SEQUENCE: 5
caagaacacg uagagaaa                                                    18

<210> SEQ ID NO 6
<211> LENGTH: 33
<212> TYPE: DNA
<213> ORGANISM: Artificial
<220> FEATURE:
<223> OTHER INFORMATION: Synthetic construct

<400> SEQUENCE: 6
gtttctctag gctagctaca acgagtgttc ttg                                   33

<210> SEQ ID NO 7
<211> LENGTH: 19
<212> TYPE: DNA
<213> ORGANISM: Artificial
<220> FEATURE:
<223> OTHER INFORMATION: Synthetic construct

<400> SEQUENCE: 7
aggugcaggg uggagagca                                                   19

<210> SEQ ID NO 8
<211> LENGTH: 33
<212> TYPE: DNA
<213> ORGANISM: Artificial
<220> FEATURE:
<223> OTHER INFORMATION: Synthetic construct

<400> SEQUENCE: 8
```

```
tgctctccag gctagctaca acgacctgca cct                                    33
```

<210> SEQ ID NO 9
<211> LENGTH: 67
<212> TYPE: DNA
<213> ORGANISM: Artificial
<220> FEATURE:
<223> OTHER INFORMATION: Synthetic construct

<400> SEQUENCE: 9

```
agacgagtct cacgcaagaa cacguagaga aacaggugca ggguggagag cagtcgtgag        60
actcgtc                                                                 67
```

<210> SEQ ID NO 10
<211> LENGTH: 24
<212> TYPE: DNA
<213> ORGANISM: Artificial
<220> FEATURE:
<223> OTHER INFORMATION: Synthetic construct

<400> SEQUENCE: 10

```
agacgagtct cacgcaagaa cacg                                              24
```

<210> SEQ ID NO 11
<211> LENGTH: 24
<212> TYPE: DNA
<213> ORGANISM: Artificial
<220> FEATURE:
<223> OTHER INFORMATION: Synthetic construct

<400> SEQUENCE: 11

```
uggagagcag tcgtgagact cgtc                                              24
```

<210> SEQ ID NO 12
<211> LENGTH: 48
<212> TYPE: DNA
<213> ORGANISM: Artificial
<220> FEATURE:
<223> OTHER INFORMATION: Synthetic construct

<400> SEQUENCE: 12

```
agacgagtct cacgcaagaa cacguggaga gcagtcgtga gactcgtc                    48
```

<210> SEQ ID NO 13
<211> LENGTH: 113
<212> TYPE: DNA
<213> ORGANISM: Artificial
<220> FEATURE:
<223> OTHER INFORMATION: Synthetic construct

<400> SEQUENCE: 13

```
tggctccgat atcacgctta ctgctctcca ccctgcacct ggtttctcta cgtgttcttg        60
cgtgatatcg gagccagatc agtcgataca tcaggtatag tgagtcgtat taa             113
```

<210> SEQ ID NO 14
<211> LENGTH: 95
<212> TYPE: DNA
<213> ORGANISM: Artificial
<220> FEATURE:
<223> OTHER INFORMATION: Synthetic construct

<400> SEQUENCE: 14

```
ccugauguau cgacugaucu ggcuccgaua ucacgcaaga acacguagag aaaccaggug        60
```
cagggtggag agcagtaagc gtgatatcgg agcca    95

<210> SEQ ID NO 15
<211> LENGTH: 45
<212> TYPE: DNA
<213> ORGANISM: Artificial
<220> FEATURE:
<223> OTHER INFORMATION: Synthetic construct

<400> SEQUENCE: 15
ccugauguau cgacugaucu ggcuccgaua ucacgcaaga acacg    45

<210> SEQ ID NO 16
<211> LENGTH: 30
<212> TYPE: DNA
<213> ORGANISM: Artificial
<220> FEATURE:
<223> OTHER INFORMATION: Synthetic construct

<400> SEQUENCE: 16
uggagagcag uaagcgugau aucggagcca    30

<210> SEQ ID NO 17
<211> LENGTH: 75
<212> TYPE: DNA
<213> ORGANISM: Artificial
<220> FEATURE:
<223> OTHER INFORMATION: Synthetic construct

<400> SEQUENCE: 17
ccugauguau cgacugaucu ggcuccgaua ucacgcaaga acacguggag agcaguaagc    60
gugauaucgg agcca    75

<210> SEQ ID NO 18
<211> LENGTH: 31
<212> TYPE: DNA
<213> ORGANISM: Artificial
<220> FEATURE:
<223> OTHER INFORMATION: Synthetic construct

<400> SEQUENCE: 18
tttctctagg ctagctacaa cgagtgttct t    31

<210> SEQ ID NO 19
<211> LENGTH: 31
<212> TYPE: DNA
<213> ORGANISM: Artificial
<220> FEATURE:
<223> OTHER INFORMATION: Synthetic construct

<400> SEQUENCE: 19
gctctccagg ctagctacaa cgacctgcac c    31

<210> SEQ ID NO 20
<211> LENGTH: 43
<212> TYPE: DNA
<213> ORGANISM: Artificial
<220> FEATURE:
<223> OTHER INFORMATION: Synthetic construct

<400> SEQUENCE: 20
gtttctctag gctagctaca acgagtgttc ttgttttttt ttt    43

<210> SEQ ID NO 21
<211> LENGTH: 43

-continued

```
<212> TYPE: DNA
<213> ORGANISM: Artificial
<220> FEATURE:
<223> OTHER INFORMATION: Synthetic construct

<400> SEQUENCE: 21
tgctctccag gctagctaca acgacctgca ccttttttt ttt                        43

<210> SEQ ID NO 22
<211> LENGTH: 1254
<212> TYPE: DNA
<213> ORGANISM: Artificial
<220> FEATURE:
<223> OTHER INFORMATION: Synthetic construct

<400> SEQUENCE: 22
atgcaccatc atcatcacca ttgttgcggt aattacgaat tactgaccac tgaaaatgcc      60
ccggtaaaaa tgtggaccaa aggcgtgccg gtagaggccg atgcgcgtca gcaacttatt     120
aatacggcga agatgccgtt tattttcaaa catattgcgg taatgcctga tgtacacctg     180
ggtaaaggtt ccaccattgg tagcgtgatc ccgaccaaag gggcgattat tccggcggcg     240
gtgggcgtgg atattggctg tggaatgaac gcgctgcgta ccgcgttaac ggcggaagac     300
ctgcctgaaa acctggcaga gctgcgtcag gcgattgaaa cggccgtgcc gcacgggcgt     360
accactggcc gttgtaaacg tgataaaggt gcctgggaaa atccaccgt taacgtcgat     420 gctaaatggg ctgagcttga agccggttat cagtggttaa cgcaaaaata tccccgtttc     480
ctgaatacca ataactataa acacctggga acgctgggaa ccgtaaacca ctttattgaa     540
atctgccttg atgagtcgga ccaggtgtgg attatgctgc actccggttc acgcggaatt     600
ggtaacgcca tcgggactta ctttatcgat ctggcacaaa aagagatgca ggaaacgctt     660
gagacgttgc cgtcgcgtga tctggcgtac tttatggaag gtacggaata ctttgatgat     720
tacctgaaag ccgtggcctg ggcgcagctt tttgccagcc ttaaccgcga tgcgatgatg     780
gaaaacgtgg taacggcatt gcagagcatt acgcagaaaa cggtcagaca gccacaaacg     840
ctggcgatgg aagagatcaa ctgtcaccac aactatgtgc aaaaagaaca gcactttggt     900
gaagagatct acgtgacgcg taaaggcgcg gtgtctgcgc gtgctggtca atatggaatt     960
attcccggtt cgatgggagc aaaaagcttt atcgtccgtg ggctgggaaa tgaagagtcg    1020
ttctgttcgt gcagccacgg tgccgggcgg gtaatgagcc gaactaaagc gaaaaaactg    1080
ttcagcgtgg aagatcaaat tcgtgccacc gcgcatgtgg aatgccgtaa agatgccgaa    1140
gtgatcgacg aaatcccgat ggcgtataaa gatattgatg cggtgatggc ggcacaaagc    1200
gatctggtgg aagttatcta taccctgcgt caggtggtgt gcgtaaaagg ataa          1254

<210> SEQ ID NO 23
<211> LENGTH: 417
<212> TYPE: PRT
<213> ORGANISM: Artificial
<220> FEATURE:
<223> OTHER INFORMATION: Synthetic construct

<400> SEQUENCE: 23

Met His His His His His His Cys Cys Gly Asn Tyr Glu Leu Leu Thr
 1               5                  10                  15

Thr Glu Asn Ala Pro Val Lys Met Trp Thr Lys Gly Val Pro Val Glu
             20                  25                  30

Ala Asp Ala Arg Gln Gln Leu Ile Asn Thr Ala Lys Met Pro Phe Ile
         35                  40                  45
```

Phe Lys His Ile Ala Val Met Pro Asp Val His Leu Gly Lys Gly Ser
    50                  55                  60

Thr Ile Gly Ser Val Ile Pro Thr Lys Gly Ala Ile Ile Pro Ala Ala
65                  70                  75                  80

Val Gly Val Asp Ile Gly Cys Gly Met Asn Ala Leu Arg Thr Ala Leu
                85                  90                  95

Thr Ala Glu Asp Leu Pro Glu Asn Leu Ala Glu Leu Arg Gln Ala Ile
            100                 105                 110

Glu Thr Ala Val Pro His Gly Arg Thr Thr Gly Arg Cys Lys Arg Asp
        115                 120                 125

Lys Gly Ala Trp Glu Asn Pro Val Asn Val Asp Ala Lys Trp Ala
    130                 135                 140

Glu Leu Glu Ala Gly Tyr Gln Trp Leu Thr Gln Lys Tyr Pro Arg Phe
145                 150                 155                 160

Leu Asn Thr Asn Asn Tyr Lys His Leu Gly Thr Leu Gly Thr Gly Asn
                165                 170                 175

His Phe Ile Glu Ile Cys Leu Asp Glu Ser Asp Gln Val Trp Ile Met
            180                 185                 190

Leu His Ser Gly Ser Arg Gly Ile Gly Asn Ala Ile Gly Thr Tyr Phe
        195                 200                 205

Ile Asp Leu Ala Gln Lys Glu Met Gln Glu Thr Leu Glu Thr Leu Pro
    210                 215                 220

Ser Arg Asp Leu Ala Tyr Phe Met Glu Gly Thr Glu Tyr Phe Asp Asp
225                 230                 235                 240

Tyr Leu Lys Ala Val Ala Trp Ala Gln Leu Phe Ala Ser Leu Asn Arg
                245                 250                 255

Asp Ala Met Met Glu Asn Val Val Thr Ala Leu Gln Ser Ile Thr Gln
            260                 265                 270

Lys Thr Val Arg Gln Pro Gln Thr Leu Ala Met Glu Glu Ile Asn Cys
        275                 280                 285

His His Asn Tyr Val Gln Lys Glu Gln His Phe Gly Glu Glu Ile Tyr
    290                 295                 300

Val Thr Arg Lys Gly Ala Val Ser Ala Arg Ala Gly Gln Tyr Gly Ile
305                 310                 315                 320

Ile Pro Gly Ser Met Gly Ala Lys Ser Phe Ile Val Arg Gly Leu Gly
                325                 330                 335

Asn Glu Glu Ser Phe Cys Ser Cys Ser His Gly Ala Gly Arg Val Met
            340                 345                 350

Ser Arg Thr Lys Ala Lys Lys Leu Phe Ser Val Glu Asp Gln Ile Arg
        355                 360                 365

Ala Thr Ala His Val Glu Cys Arg Lys Asp Ala Glu Val Ile Asp Glu
    370                 375                 380

Ile Pro Met Ala Tyr Lys Asp Ile Asp Ala Val Met Ala Ala Gln Ser
385                 390                 395                 400

Asp Leu Val Glu Val Ile Tyr Thr Leu Arg Gln Val Val Cys Val Lys
                405                 410                 415

Gly

<210> SEQ ID NO 24
<211> LENGTH: 14
<212> TYPE: DNA
<213> ORGANISM: Artificial
<220> FEATURE:
<223> OTHER INFORMATION: Synthetic construct

```
<400> SEQUENCE: 24
tccgagccgg acga                                                       14

<210> SEQ ID NO 25
<211> LENGTH: 11
<212> TYPE: DNA
<213> ORGANISM: Artificial
<220> FEATURE:
<223> OTHER INFORMATION: Synthetic construct

<400> SEQUENCE: 25
gtgaccccuu g                                                          11

<210> SEQ ID NO 26
<211> LENGTH: 19
<212> TYPE: DNA
<213> ORGANISM: Artificial
<220> FEATURE:
<223> OTHER INFORMATION: Synthetic construct

<400> SEQUENCE: 26
ucaugcagcg cguaguguc                                                  19

<210> SEQ ID NO 27
<211> LENGTH: 18
<212> TYPE: DNA
<213> ORGANISM: Artificial
<220> FEATURE:
<223> OTHER INFORMATION: Synthetic construct

<400> SEQUENCE: 27
ugaugcagcg cauguguc                                                   18

<210> SEQ ID NO 28
<211> LENGTH: 13
<212> TYPE: DNA
<213> ORGANISM: Artificial
<220> FEATURE:
<223> OTHER INFORMATION: Synthetic construct

<400> SEQUENCE: 28
aagcaguuaa gac                                                        13
```

PARTICLES COATED WITH CATALYSTS USEFUL FOR SPLICING NUCLEIC ACIDS

CROSS REFERENCE TO RELATED APPLICATIONS

This application claims the benefit of U.S. Provisional Application No. 62/581,422 filed Nov. 3, 2017. The entirety of this application is hereby incorporated by reference for all purposes.

STATEMENT REGARDING FEDERALLY FUNDED RESEARCH

This invention was made with government support under GM124472 and GM097399 awarded by the National Institutes of Health and 1350829 awarded by the National Science Foundation. The government has certain rights in the invention.

INCORPORATION-BY-REFERENCE OF MATERIAL SUBMITTED AS A TEXT FILE VIA THE OFFICE ELECTRONIC FILING SYSTEM (EFS-WEB)

The Sequence Listing associated with this application is provided in text format in lieu of a paper copy, and is hereby incorporated by reference into the specification. The name of the text file containing the Sequence Listing is 18022US_ST25.txt. The text file is 4 KB, was created on Nov. 5, 2018, and is being submitted electronically via EFS-Web.

BACKGROUND

Genetic diseases such as cystic fibrosis are difficult to treat. Gene therapy-based strategies show promise. Gene therapy may consist of altering the sequence of a defective gene (DNA) or the corresponding mRNA (mRNA editing) to produce a functioning protein. Gene editing may pose a risk of creating cancerous cells. See Haapaniemi et al. CRISPR—Cas9 genome editing induces a p53-mediated DNA damage response. Nature Medicine, volume 24, pages 927-930 (2018). Thus, there is a need to identify improvements.

Yehl, et al. report catalytic deoxyribozyme-modified nanoparticles for RNAi-independent gene regulation. ACS Nano, 2012, 6, 9150-9157. See also U.S. Pat. No. 9,803,197; Yang et al., Chem Commun, 2010, 46, 3107-3109; Liu & Lu, Chem Mater, 2004, 16, 3231-3238; Rosi et al., Science 2006, 312, 1027-1030; and Giljohann et al., J Am Chem Soc, 2009, 131, 2072-2073. References cited herein are not an admission of prior art.

SUMMARY

This disclosure relates to compositions comprising particles conjugated to one or more catalytically cleaving nucleic acids and optionally an RNA ligating enzyme. In certain embodiments, the particle is a nanoparticle. In certain embodiments, particles reported herein are used for splicing nucleic acid sequences.

In certain embodiments, this disclosure relates to compositions comprising a particle comprising; i) a first site-specific RNA cleaving nucleic acid, and ii) a second site-specific RNA cleaving nucleic acid. In certain embodiments, the first site-specific RNA cleaving nucleic acid comprises a cleaving sequence flanked on a 3' end with a first sequence that hybridizes to a first target sequence and flanked on the 5' end with a second sequence that hybridizes to a second target sequence. In certain embodiments, a first single nucleotide is between the first target sequence and the second target sequence. In certain embodiments, a polynucleotide between 2 to 4 nucleotides is between the first target sequence and the second target sequence. In certain embodiments, the second site specific RNA cleaving nucleic acid comprises a cleaving sequence flanked on the a 3' end with a third sequence that hybridizes to a third target sequence and flanked on the 5' end with a fourth sequence that hybridizes to a fourth target sequence. In certain embodiments, a second single nucleotide is between the third target sequence and the fourth target sequence. In certain embodiments, a polynucleotide between 2 to 4 nucleotides is between the third target sequence and the fourth target sequence.

In certain embodiments, this disclosure relates to compositions comprising a particle comprising; i) a first site-specific RNA cleaving nucleic acid, ii) a second site-specific RNA cleaving nucleic acid, and iii) a ligase enzyme. In certain embodiments, the first site-specific RNA cleaving nucleic acid comprises a cleaving sequence flanked on a 3' end with a first sequence that hybridizes to a first target sequence and flanked on the 5' end with a second sequence that hybridizes to a second target sequence. In certain embodiments, a first single nucleotide is between the first target sequence and the second target sequence. In certain embodiments, a polynucleotide between 2 to 4 nucleotides is between the first target sequence and the second target sequence. In certain embodiments, the second site specific RNA cleaving nucleic acid comprises a cleaving sequence flanked on the a 3' end with a third sequence that hybridizes to a third target sequence and flanked on the 5' end with a fourth sequence that hybridizes to a fourth target sequence. In certain embodiments, a second single nucleotide is between the third target sequence and the fourth target sequence. In certain embodiments, a polynucleotide between 2 to 4 nucleotides is between the third target sequence and the fourth target sequence.

In certain embodiments, the first and second RNA cleaving nucleic acids are attached to the particle through direct conjugation on the 3' end or hybridization to a segment on the 3' end.

In certain embodiments, the first site-specific RNA cleaving nucleic acid comprises GGCTAGCTACAACGA (SEQ ID NO: 2) flanked on the 3' end with the first sequence and the 5' end with the second sequence. In certain embodiments, the second site-specific RNA cleaving nucleic acid comprises GGCTAGCTACAACGA (SEQ ID NO: 2) flanked on the 3' end with the third sequence and the 5' end with the fourth sequence.

In certain embodiments, the first or second target sequence are not identical to the third or fourth target sequence. In certain embodiments, the first and second target sequence are not identical to the third and fourth target sequence.

In certain embodiments, the particle is a metal nanoparticle. In certain embodiments, the metal is gold, silver, iron, or copper.

In certain embodiments, the RNA ligating enzyme is an RNA cyclase B (RtcB).

In certain embodiments, the ligating enzyme comprises a cysteine, dicysteine, or polycysteine flanked on the N-terminal end or C-terminal end. In certain embodiments, the ligating enzyme comprises 5'-CCGNYELLT- TENAPVKMWTKGVPVEADARQQLIN-
TAKMPFIFKHIAVMPDVHLGKG STIGSVIPTKGAII-
PAAVGVDIGCGMNALRTALTAEDLPENLAELRQAIE
TAVPHGRTTGR CKRDKGAWENPPVNVDAKWAEL-
EAGYQWLTQKYPRFLNTNNYKHLGTLGTGNHFIEI
CLDESDQVWIMLHSGSRGIGNAIGTYFID-
LAQKEMQETLETLPSRDLAYFMEGTEYFDD
YLKAVAWAQLFASLNRDAM-
MENVVTALQSITQKTVRQPQTLAMEEINCH-
HNYVQKEQ HFGEEIYVTRKGAVSARAGQY-
GIIPGSMGAKSFIVRGLGNEESFCSCSHGAGRVMSRTK
AKKLFSVEDQIRATAHVECRKDAEVIDEIPMAYKDI-
DAVMAAQSDLVEVIYTLRQVVCV KG (SEQ ID NO: 1)
or variants thereof.

In certain embodiments, this disclosure relates to compositions comprising a ligase enzyme and a particle comprising; i) a first site-specific RNA cleaving nucleic acid, and ii) a second site-specific RNA cleaving nucleic acid. In certain embodiments, the first site-specific RNA cleaving nucleic acid comprises a cleaving sequence flanked on a 3' end with a first sequence that hybridizes to a first target sequence and flanked on the 5' end with a second sequence that hybridizes to a second target sequence. In certain embodiments, a first single nucleotide is between the first target sequence and the second target sequence. In certain embodiments, a polynucleotide between 2 to 4 nucleotides is between the first target sequence and the second target sequence. In certain embodiments, the second site specific RNA cleaving nucleic acid comprises a cleaving sequence flanked on the a 3' end with a third sequence that hybridizes to a third target sequence and flanked on the 5' end with a fourth sequence that hybridizes to a fourth target sequence. In certain embodiments, a second single nucleotide is between the third target sequence and the fourth target sequence. In certain embodiments, a polynucleotide between 2 to 4 nucleotides is between the third target sequence and the fourth target sequence. In certain embodiments, the first or second target sequence are not identical to the third or fourth target sequence.

In certain embodiments, this disclosure relates to methods of splicing RNA comprising mixing a particle comprising; i) a first site-specific RNA cleaving nucleic acid, ii) a second site-specific RNA cleaving nucleic acid, and iii) a ligase enzyme, wherein the first site-specific RNA cleaving nucleic acid comprises a cleaving sequence flanked on a 3' end with a first sequence that hybridizes to a first target sequence and flanked on the 5' end with a second sequence that hybridizes to a second target sequence; wherein the second site specific RNA cleaving nucleic acid comprises a cleaving sequence flanked on the a 3' end with a third sequence that hybridizes to a third target sequence and flanked on the 5' end with a fourth sequence that hybridizes to a fourth target sequence; with a nucleic acid comprising the first target sequence, the second target sequence, the third target sequence, and the four target sequence under conditions such that a spliced RNA is formed comprising the first target sequence joined to the fourth target sequence wherein the spliced RNA does not contain the second and third target sequences. In certain embodiments, mixing a particle with a nucleic acid further comprises mixing a ligase enzyme with the particle and with the nucleic acid.

In certain embodiments, this disclosure relates to methods of splicing RNA comprising mixing a ligase enzyme and a particle comprising; i) a first site-specific RNA cleaving nucleic acid and ii) a second site-specific RNA cleaving nucleic acid, wherein the first site-specific RNA cleaving nucleic acid comprises a cleaving sequence flanked on a 3' end with a first sequence that hybridizes to a first target sequence and flanked on the 5' end with a second sequence that hybridizes to a second target sequence; wherein the second site specific RNA cleaving nucleic acid comprises a cleaving sequence flanked on the a 3' end with a third sequence that hybridizes to a third target sequence and flanked on the 5' end with a fourth sequence that hybridizes to a fourth target sequence; with a nucleic acid comprising the first target sequence, the second target sequence, the third target sequence, and the four target sequence under conditions such that a spliced RNA is formed comprising the first target sequence joined to the fourth target sequence wherein the spliced RNA does not contain the second and third target sequences.

In certain embodiments, the first or second target sequence are not identical to the third or fourth target sequence. In certain embodiments, the first and second target sequence are not identical to the third and fourth target sequence.

In certain embodiments, this disclosure relates to a ligating enzyme comprising a cysteine, dicysteine, or polycysteine flanked on the N-terminal end or C-terminal end. In certain embodiments, the ligating enzyme comprising a dicysteine comprises 5'-CCGNYELLT-
TENAPVKMWTKGVPVEADARQQLIN-
TAKMPFIFKHIAVMPDVHLGKG STIGSVIPTKGAII-
PAAVGVDIGCGMNALRTALTAEDLPENLAELRQAIE
TAVPHGRTTGR CKRDKGAWENPPVNVDAKWAEL-
EAGYQWLTQKYPRELNTNNYKHLGTLGTGNHFIEI
CLDESDQVWIMLHSGSRGIGNAIGTYFID-
LAQKEMQETLETLPSRDLAYFMEGTEYFDD
YLKAVAWAQLFASLNRDAM-
MENVVTALQSITQKTVRQPQTLAMEEINCH-
HNYVQKEQ HFGEEIYVTRKGAVSARAGQY-
GIIPGSMGAKSFIVRGLGNEESFCSCSHGAGRVMSRTK
AKKLFSVEDQIRATAHVECRKDAEVIDEIPMAYKDI-
DAVMAAQ SDLVEVIYTLRQVVCV KG (SEQ ID NO: 1)
or variants thereof.

In certain embodiments, this disclosure relates to nucleic acids encoding a recombinant ligating enzyme disclosed herein optionally in operable combination with a promoter. In certain embodiments, this disclosure relates to vector comprising a nucleic acid disclosed herein. In certain embodiments, this disclosure relates to expression systems comprising a nucleic acid or vector disclosed herein such as a cell.

In certain embodiments, the nucleic acids are DNAzymes that cleave RNA. In certain embodiments, the DNAzyme is 10-23 DNAzyme. In certain embodiments, DNAzymes target two or more specific RNA sequences. In certain embodiments, the particle is conjugated to the nucleic acid through a linking group on the 3' end comprising a thiol group, metal ligand, ethylene glycol polymer, alkyl chain, ester group, or amide group.

In certain embodiments, the ligating enzyme is RtcB. In certain embodiments, the RNA ligase may be in solution rather than attached to the particle.

In certain embodiments, this disclosure relates to methods of manufacturing a particle disclosed herein; in certain embodiments, alternative methods of manufacturing may be used.

In certain embodiments, this disclosure relates to methods for modifying RNA using a particle comprising a metallic nanoparticle core conjugated to two catalytic nucleic acid strands and an RNA ligase. In other embodiments, this disclosure relates to methods for removing or excising specific segments of nucleotides from a target RNA using a particle as described above.

In certain embodiments, the particle as described above is used to modify RNAs in vitro, in other embodiments the particle as described above is used to modify RNAs in vivo including in humans.

BRIEF DESCRIPTION OF THE DRAWINGS

FIG. 1E illustrates constructs, cleaved and spliced products (SEQ ID NOs: 9-12) that were used and identified in experiments reported herein.

FIG. 1F illustrates constructs, cleaved and spliced products (SEQ ID NOs: 13-17) that were used and identified in experiments reported herein.

DETAILED DISCUSSION

Figure 1A:
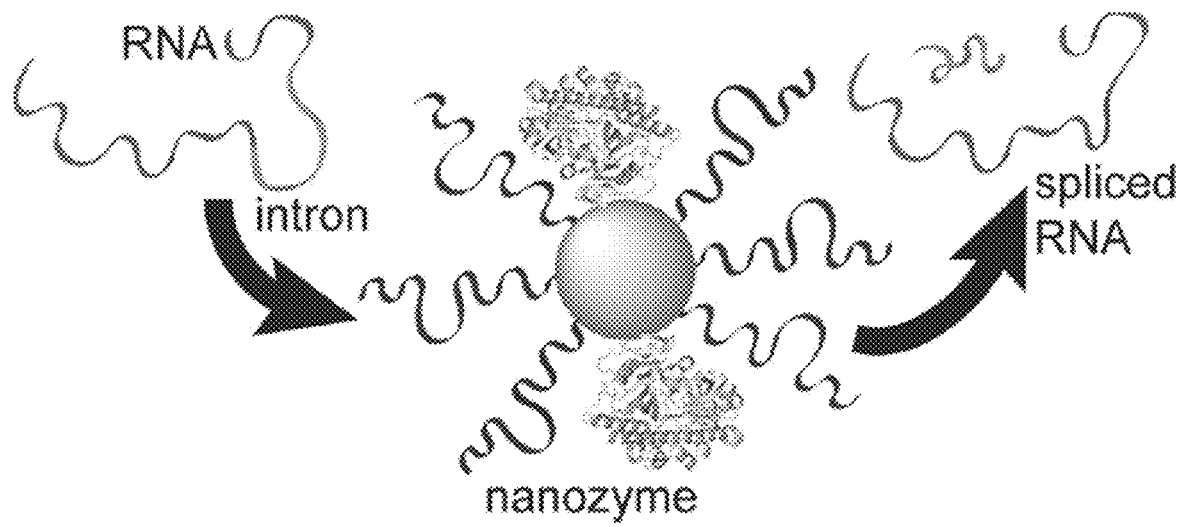
FIG. 1A illustrates a method disclosed herein wherein a nanozyme is capable of splicing an RNA stem—loop. This nanozyme is comprised of a gold nanoparticle functionalized with three enzymes: two catalytic nucleic acid strands with ribonuclease cleaving function and an RNA ligase. The nanozyme cleaves and then ligates RNA targets, performing a splicing reaction that is akin to the function of the spliceosome. The three-enzyme reaction can remove a 19 nt segment from a 67 nt RNA loop.
Figure 1B:
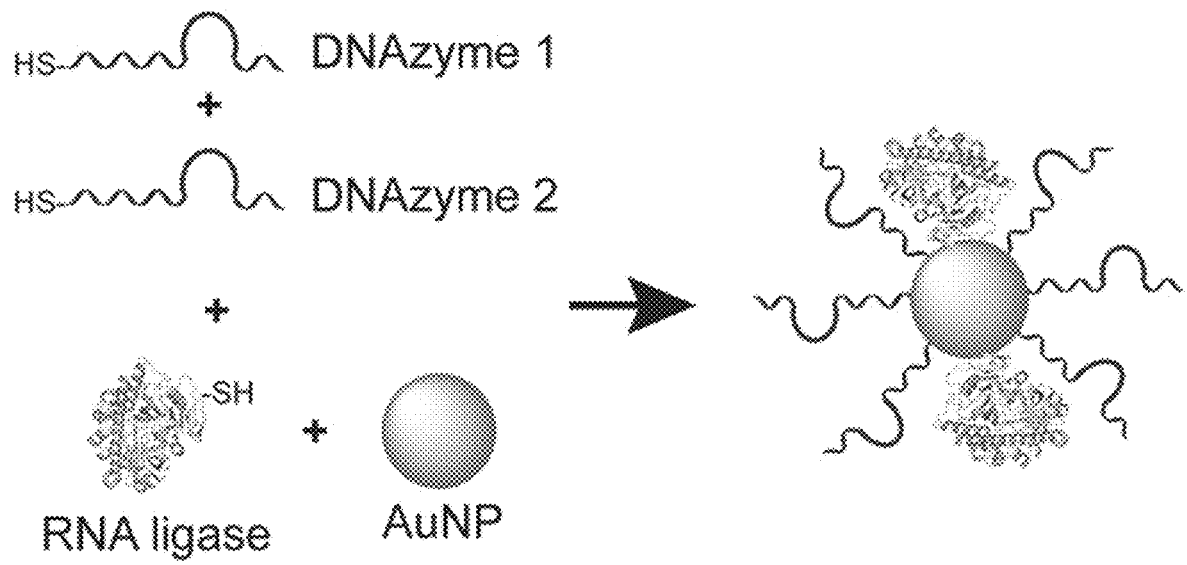
FIG. 1B illustrates the preparation of a particle disclosed herein. Experiment reported herein indicate that DNAzymes and RtcB can work together in an RNA splicing reaction. Nanozymes are constructed of two DNAzymes and an RNA ligase (RtcB) attached to a gold nanoparticle (AuNP) scaffold.
Figure 1C:
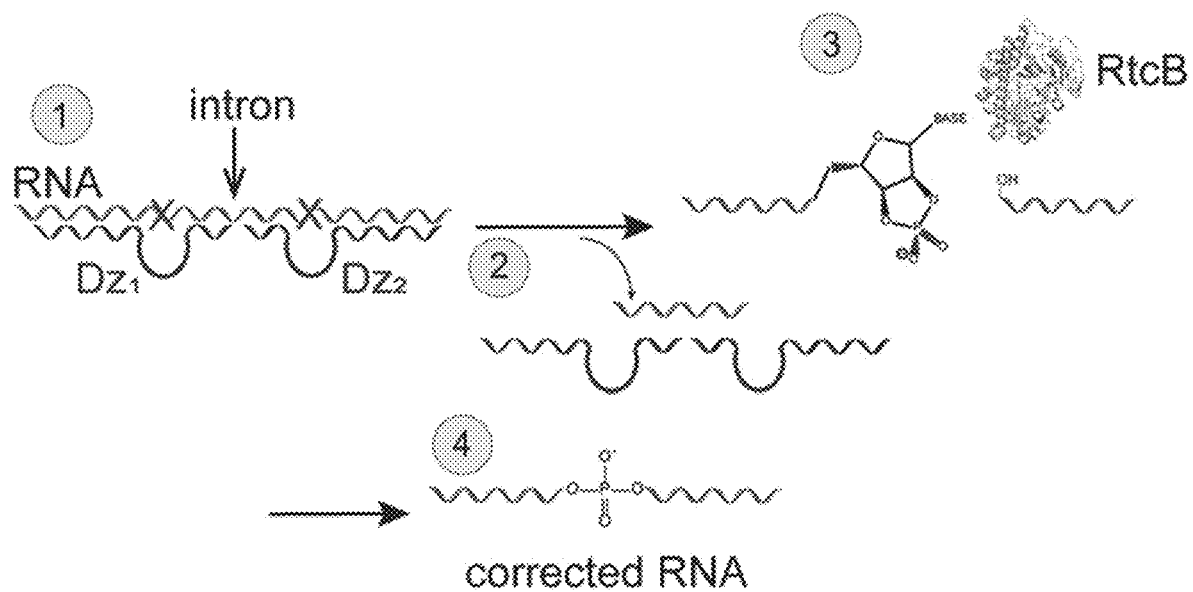
FIG. 1C illustrates that DNAzymes cleave target RNA at purine/pyrimidine junctions ("X"), removing an intron and leaving 2'-3'-cyclic phosphates that RtcB can ligate to produce corrected RNA. Crystal structure is from the *P. horikoshii* RtcB species as reported in Desai et al. Structures of the Noncanonical RNA Ligase RtcB Reveal the Mechanism of Histidine Guanylylation. Biochemistry 2013, 52, 2518-25.
Figure 1D:
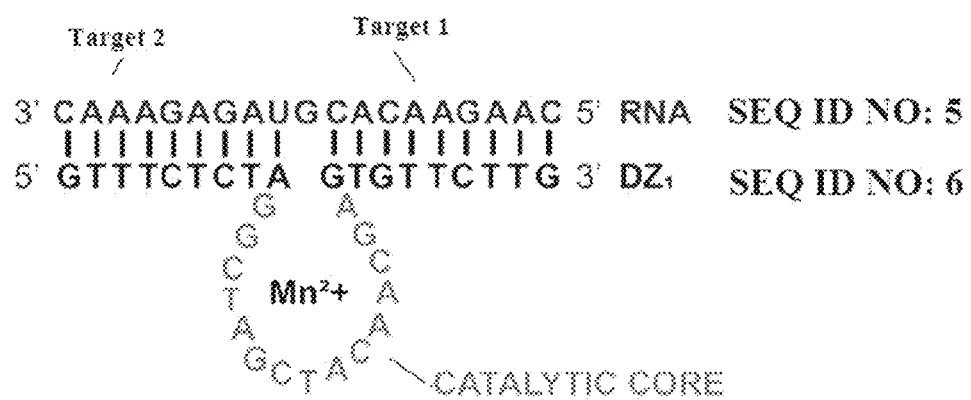
FIG. 1D illustrates sequences that may be used in the splicing reaction illustrated in FIG. 1C. The first site-specific RNA cleaving nucleic acid, Top (SEQ ID NO: 6), comprises a cleaving sequence 5'-GGCTAGCTACAACGA (SEQ ID NO: 2) flanked on a 3' end with a first sequence that hybridizes to a first target sequence 5'-CAAGAACAC (SEQ ID NO: 3) and flanked on the 5' end with a second sequence that hybridizes to a second target sequence. A first single nucleotide (G) is between the first target sequence and the second target sequence to provide SEQ ID NO: 5. The second site specific RNA cleaving nucleic acid, Bottom (SEQ ID NO: 8), comprises a cleaving sequence 5'-GGCTAGCTACAACGA (SEQ ID NO: 2) flanked on the a 3' end with a third sequence that hybridizes to a third target sequence and flanked on the 5' end with a fourth sequence that hybridizes to a fourth target sequence 5'-UGGAGAGCA (SEQ ID NO: 4). A second single nucleotide (G) is between the third target sequence and the fourth target sequence to provide SEQ ID NO: 7.
Figure 1D:
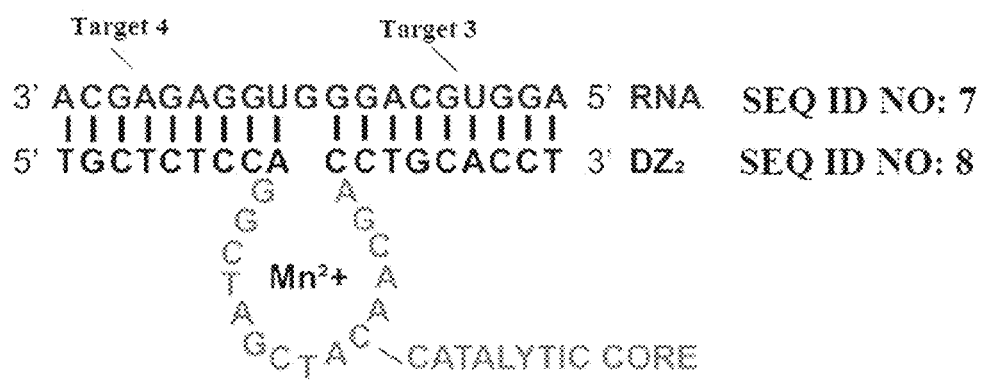

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

A "nucleic acid," or "oligonucleotide," is defined as a polymer of nucleotides. As used herein, a "nucleotide" is given its ordinary meaning as used in the art, i.e., a molecule comprising a sugar moiety, a phosphate group, and a base (usually nitrogenous). Typically, the nucleotide comprises one or more bases connected to a sugar-phosphate backbone (a base connected only to a sugar moiety, without the phosphate group, is a "nucleoside"). The sugars within the nucleotide can be, for example, ribose sugars (a "ribonucleic acid," or "RNA"), or deoxyribose sugars (a "deoxyribonucleic acid," or "DNA"). In some cases, the polymer can comprise both ribose and deoxyribose sugars. Examples of bases include, but not limited to, the naturally occurring bases (e.g., adenosine or "A," thymidine or "T," guanosine or "G," cytidine or "C," or uridine or "U"). In some cases, the polymer can also comprise nucleoside analogs (e.g., aracytidine, inosine, isoguanosine, nebularine, pseudouridine, 2,6-diaminopurine, 2-aminopurine, 2-thiothymidine, 3-deaza-5-azacytidine, 2'-deoxyuridine, 3-nitorpyrrole, 4-methylindole, 4-thiouridine, 4-thiothymidine, 2-aminoadenosine, 2-thiothymidine, 2-thiouridine, 5-bromocytidine, 5-iodouridine, inosine, 6-azauridine, 6-chloropurine, 7-deazaadenosine, 7-deazaguanosine, 8-azaadenosine, 8-azidoadenosine, benzimidazole, N1-methyladenosine, pyrrolo-pyrimidine, 2-amino-6-chloropurine, 3-methyl adenosine, 5-propynylcytidine, 5-propynyluridine, 5-bromouridine, 5-fluorouridine, 5-methylcytidine, 7-deazaadenosine, 7-deazaguanosine, 8-oxoadenosine, 8-oxoguanosine, 6-O-methylguanine, 2-thiocytidine, etc.), chemically or biologically modified bases (e.g., methylated bases), intercalated bases, modified sugars (e.g., 2'-fluororibose, 2'-aminoribose, 2'-azidoribose, 2'-O-methylribose, L-enantiomeric nucleosides arabinose, hexose, etc.), modified phosphate moieties (e.g., phosphorothioates or 5'-N-phosphoramidite linkages), and/or other naturally and non-naturally occurring bases substitutable into the polymer, including substituted and unsubstituted aromatic moieties. A nucleic acid sequence may be composed of DNA nucleotides, RNA nucleotides or a combination of both types.

A nucleic acid sequence may also include natural nucleotides, chemically modified nucleotides, and synthetic nucleotides such as arabino nucleic acids (ANA); 2'-fluoroarabino nucleic acids (FANA); hexitol nucleic acids (HNA); and cyclohexene nucleic acids (CeNA). In certain embodiments, the nucleic acid sequence comprises monomers of phosphodiester, phosphorothioate, methylphosphonate, phosphorodiamidate, piperazine phosphorodiamidate, ribose, 2'-O-methy ribose, 2'-O-methoxyethyl ribose, 2'-fluororibose, deoxyribose, 1-(hydroxymethyl)-2,5-dioxabicyclo[2.2.1]heptan-7-ol, 1-(hydroxymethyl)-2,5-dioxabicyclo[2.2.1]heptan-7-yl phosphate, O-(1-(hydroxymethyl)-2,5-dioxabicyclo[2.2.1]heptan-7-yl) phosphorothioate, 5-(hydroxymethyl)-2,6-dioxa-3-azabicyclo[3.2.1]octan-8-ol, 5-(hydroxymethyl)-2,6-dioxa-3-azabicyclo[3.2.1]octan-8-yl phosphate, O-(5-(hydroxymethyl)-2,6-dioxa-3-azabicyclo [3.2.1]octan-8-yl) phosphorothioate, P-(2-(hydroxymethyl)morpholino)-N,N-dimethylphosphoramidate, morpholin-2-ylmethanol, (2-(hydroxymethyl) morpholino) (piperazin-1-yl)phosphinate, or peptide nucleic acids or combinations thereof.

In certain embodiments, the disclosure relates to cleaving nucleic acids comprising locked nucleic acids. As used herein, a "locked nucleic acid" to synthetic nucleotides that contain bicyclic monomers. Nucleotides are conformationally locked when the ribose ring is connected by a methylene bridge (blue) between the 2'-O and 4'-C atoms; thus, "locking" the ribose ring to form a dioxabicyclic rings. Examples include 2', 4'-C methylene bicyclo nucleotides and 2'-0,4'-C-aminomethylene bridged nucleotides (see for example U.S. Pat. Nos. 6,639,059, 6,670,461, 7,053,207, and 7,427,672). Locked nucleic acids may consist of a mixture of locked nucleotides and unlocked nucleotides, e.g., with ribose ring(s) that are not bicyclic as in naturally occurring nucleic acids. Inserting bicyclic monomers into a nucleobase polymer alters interactions with naturally occurring enzymes that degrade oligonucleotides. Thus, by altering nucleobase polymers to contain locked and unlocked nucleobases one may prevent natural enzymes, such as RNase H1, from cleaving the nucleic acid hybridized to naturally occurring RNA or DNA. Locked nucleic acid may also contain a phosphorothioate-modified backbone, partially or fully, which further prevents degradation.

The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "vector" or "expression vector" refer to a recombinant nucleic acid containing a desired coding sequence and appropriate nucleic acid sequences necessary for the expression of the operably linked coding sequence in a particular host organism or expression system, e.g., cellular or cell-free. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

Protein "expression systems" refer to in vivo and in vitro (cell free) systems. Systems for recombinant protein expression typically utilize cells transfecting with a DNA expression vector that contains the template. The cells are cultured under conditions such that they translate the desired protein. Expressed proteins are extracted for subsequent purification. In vivo protein expression systems using prokaryotic and eukaryotic cells are well known. Also, some proteins are recovered using denaturants and protein-refolding procedures. In vitro (cell-free) protein expression systems typically use translation-compatible extracts of whole cells or compositions that contain components sufficient for transcription, translation and optionally post-translational modifications such as RNA polymerase, regulatory protein factors, transcription factors, ribosomes, tRNA cofactors, amino acids and nucleotides. In the presence of an expression vectors, these extracts and components can synthesize proteins of interest. Cell-free systems typically do not contain proteases and enable labelling of the protein with modified amino acids. Some cell free systems incorporated encoded components for translation into the expression vector. See, e.g., Shimizu et al., Cell-free translation reconstituted with purified components, 2001, Nat. Biotechnol., 19, 751-755 and Asahara & Chong, Nucleic Acids Research, 2010, 38(13): e141, both hereby incorporated by reference in their entirety.

A "selectable marker" is a nucleic acid introduced into a vector that encodes a polypeptide that confers a trait suitable for artificial selection or identification (report gene), e.g., beta-lactamase confers antibiotic resistance, which allows an organism expressing beta-lactamase to survive in the presence antibiotic in a growth medium. Another example is thymidine kinase, which makes the host sensitive to ganciclovir selection. It may be a screenable marker that allows one to distinguish between wanted and unwanted cells based on the presence or absence of an expected color. For example, the lac-z-gene produces a beta-galactosidase enzyme which confers a blue color in the presence of X-gal (5-bromo-4-chloro-3-indolyl-β-D-galactoside). If recombinant insertion inactivates the lac-z-gene, then the resulting colonies are colorless. There may be one or more selectable markers, e.g., an enzyme that can complement to the inability of an expression organism to synthesize a particular compound required for its growth (auxotrophic) and one able to convert a compound to another that is toxic for growth. URA3, an orotidine-5' phosphate decarboxylase, is necessary for uracil biosynthesis and can complement ura3 mutants that are auxotrophic for uracil. URA3 also converts 5-fluoroorotic acid into the toxic compound 5-fluorouracil. Additional contemplated selectable markers include any genes that impart antibacterial resistance or express a fluorescent protein. Examples include, but are not limited to, the following genes: ampr, camr, tetr, blasticidinr, neor, hygr, abxr, neomycin phosphotransferase type II gene (nptII), p-glucuronidase (gus), green fluorescent protein (gfp), egfp, yfp, mCherry, p-galactosidase (lacZ), lacZa, lacZAM15, chloramphenicol acetyltransferase (cat), alkaline phosphatase (phoA), bacterial luciferase (luxAB), bialaphos resistance gene (bar), phosphomannose isomerase (pmi), xylose isomerase (xylA), arabitol dehydrogenase (atlD), UDP-glucose:galactose-1-phosphate uridyltransferasel (galT), feedback-insensitive α subunit of anthranilate synthase (OASA1D), 2-deoxyglucose (2-DOGR), benzyladenine-N-3-glucuronide, E. coli threonine deaminase, glutamate 1-semialdehyde aminotransferase (GSA-AT), D-amino acidoxidase (DAAO), salt-tolerance gene (rstB), ferredoxin-like protein (pflp), trehalose-6-P synthase gene (AtTPS1), lysine racemase (lyr), dihydrodipicolinate synthase (dapA), tryptophan synthase beta 1 (AtTSB1), dehalogenase (dhlA), mannose-6-phosphate reductase gene (M6PR), hygromycin phosphotransferase (HPT), and D-serine ammonialyase (dsdA).

A "label" refers to a detectable compound or composition that is conjugated directly or indirectly to another molecule, such as an enzyme, protein, or nucleic acid, to facilitate detection of that molecule. Specific, non-limiting examples of labels include fluorescent tags, enzymatic linkages, and radioactive isotopes. A label includes the incorporation of a radiolabelled amino acid or the covalent attachment of biotinyl moieties to a polypeptide that can be detected by marked avidin (for example, streptavidin containing a fluorescent marker or enzymatic activity that can be detected by optical or colorimetric methods). Various methods of labelling polypeptides and glycoproteins are known in the art and may be used. Examples of labels for polypeptides include, but are not limited to, the following: radioisotopes or radionucleotides (such as $^{35}S$ or $^{131}I$) fluorescent labels (such as fluorescein isothiocyanate (FITC), rhodamine, lanthanide phosphors), enzymatic labels (such as horseradish peroxidase, beta-galactosidase, luciferase, alkaline phosphatase), chemiluminescent markers, biotinyl groups, predetermined polypeptide epitopes recognized by a secondary reporter (such as a leucine zipper pair sequences, binding sites for secondary antibodies, metal binding domains, epitope tags), or magnetic agents, such as gadolinium chelates. In some embodiments, labels are attached by spacer arms of various lengths to reduce potential steric hindrance.

In certain embodiments, the disclosure relates to the vectors comprising a nucleic acid encoding a peptide disclosed herein or chimeric protein thereof.

In certain embodiments, the vector optionally comprises a mammalian, human, insect, viral, bacterial, bacterial plasmid, yeast associated origin of replication or gene such as a gene or retroviral gene or lentiviral LTR, TAR, RRE, PE, SLIP, CRS, and INS nucleotide segment or gene selected from tat, rev, nef, vif, vpr, vpu, and vpx or structural genes selected from gag, pol, and env.

In certain embodiments, the vector optionally comprises a gene vector element (nucleic acid) such as a selectable marker region, lac operon, a CMV promoter, a hybrid chicken B-actin/CMV enhancer (CAG) promoter, tac promoter, T7 RNA polymerase promoter, SP6 RNA polymerase promoter, SV40 promoter, internal ribosome entry site (IRES) sequence, cis-acting woodchuck post regulatory regulatory element (WPRE), scaffold-attachment region (SAR), inverted terminal repeats (ITR), FLAG tag coding region, c-myc tag coding region, metal affinity tag coding region, streptavidin binding peptide tag coding region, polyHis tag coding region, HA tag coding region, MBP tag coding region, GST tag coding region, polyadenylation coding region, SV40 polyadenylation signal, SV40 origin of replication, Col E1 origin of replication, f1 origin, pBR322 origin, or pUC origin, TEV protease recognition site, loxP site, Cre recombinase coding region, or a multiple cloning site such as having 5, 6, or 7 or more restriction sites within a continuous segment of less than 50 or 60 nucleotides or having 3 or 4 or more restriction sites with a continuous segment of less than 20 or 30 nucleotides.

"Amino acid sequence" is defined as a sequence composed of any one of the 20 naturally appearing amino acids, amino acids that have been chemically modified, or composed of synthetic amino acids. The terms "protein" and "peptide" refer to compounds comprising amino acids joined via peptide bonds and are used interchangeably. As used herein, where "amino acid sequence" is recited herein to refer to an amino acid sequence of a protein molecule. An "amino acid sequence" can be deduced from the nucleic acid sequence encoding the protein.

In certain embodiments, the disclosure relates to peptides and ligating enzymes reported herein comprising sequences disclosed herein or variants or fusions thereof wherein the amino terminal end or the carbon terminal end of the amino acid sequence are optionally attached to a heterologous amino acid sequence, label, or reporter molecule.

The term "variants" is contemplated to include functional variants, allelic variants, or active fragments. Variants may include 1 or 2 amino acid substitutions or conserved substitutions. Variants may include 3 or 4 amino acid substitutions or conserved substitutions. Variants may include 5 or 6 or more amino acid substitutions or conserved substitutions. Variant include those with not more than 1% or 2% of the amino acids are substituted. Variant include those with not more than 3% or 4% of the amino acids are substituted. Variants include proteins with greater than 80%, 89%, 90%, 95%, 98%, or 99% identity or similarity.

Variants can be tested by mutating the vector to produce appropriate codon alternatives for polypeptide translation. Active variants and fragments can be identified with a high probability using computer modeling. Shihab et al. report an online genome tolerance browser. BMC Bioinformatics. 2017, 18(1):20. Ng et al. report methods of predicting the effects of amino acid substitutions on protein function. Annu Rev Genomics Hum Genet. 2006, 7:61-80. Teng et al. Approaches and resources for prediction of the effects of non-synonymous single nucleotide polymorphism on protein function and interactions. Curr Pharm Biotechnol. 2008, 9(2):123-33.

Guidance in determining which and how many amino acid residues may be substituted, inserted or deleted without abolishing biological activity may be found using computer programs well known in the art, for example, RaptorX, ESyPred3D, HHpred, Homology Modeling Professional for HyperChem, DNAStar, SPARKS-X, EVfold, Phyre, and Phyre2 software. See also Saldano et al. Evolutionary Conserved Positions Define Protein Conformational Diversity, PLoS Comput Biol. 2016, 12(3):e1004775; Marks et al. Protein structure from sequence variation, Nat Biotechnol. 2012, 30(11):1072-80; Mackenzie et al. Curr Opin Struct Biol. 2017, 44:161-167 Mackenzie et al. Proc Natl Acad Sci USA. 113(47):E7438-E7447 (2016); Joseph et al. J R Soc Interface. 2014, 11(95):20131147, Wei et al. Int. J. Mol. Sci. 2016, 17(12), 2118. Variants can be tested in functional assays. Certain variants have less than 10%, and preferably less than 5%, and still more preferably less than 2% changes (whether substitutions, deletions, and so on).

In certain embodiments, sequence "identity" refers to the number of exactly matching amino acids (expressed as a percentage) in a sequence alignment between two sequences of the alignment calculated using the number of identical positions divided by the greater of the shortest sequence or the number of equivalent positions excluding overhangs wherein internal gaps are counted as an equivalent position. For example, the polypeptides GGGGGG and GGGGT have a sequence identity of 4 out of 5 or 80%. For example, the polypeptides GGGPPP and GGGAPPP have a sequence identity of 6 out of 7 or 85%. In certain embodiments, any recitation of sequence identity expressed herein may be substituted for sequence similarity. Percent "similarity" is used to quantify the similarity between two sequences of the alignment. This method is identical to determining the identity except that certain amino acids do not have to be identical to have a match. Amino acids are classified as matches if they are among a group with similar properties according to the following amino acid groups: Aromatic—F Y W; hydrophobic—A V I L; Charged positive: R K H; Charged negative—D E; Polar—S T N Q. The amino acid groups are also considered conserved substitutions.

The term "comprising" in reference to a peptide having an amino acid sequence refers a peptide that may contain additional N-terminal (amine end) or C-terminal (carboxylic acid end) amino acids, i.e., the term is intended to include the amino acid sequence within a larger peptide. The term "consisting of" in reference to a peptide having an amino acid sequence refers a peptide having the exact number of amino acids in the sequence and not more or having not more than a rage of amino acids expressly specified in the claim. In certain embodiments, the disclosure contemplates that the "N-terminus of a peptide may consist of an amino acid sequence," which refers to the N-terminus of the peptide having the exact number of amino acids in the sequence and not more or having not more than a rage of amino acids specified in the claim however the C-terminus may be connected to additional amino acids, e.g., as part of a larger peptide. Similarly, the disclosure contemplates that the "C-terminus of a peptide may consist of an amino acid sequence," which refers to the C-terminus of the peptide having the exact number of amino acids in the sequence and not more or having not more than a rage of amino acids specified in the claim however the N-terminus may be connected to additional amino acids, e.g., as part of a larger peptide.

Particles Conjugated to Cleaving Nucleic Acids

In certain embodiments, the disclosure relates to particles conjugated to a cleaving nucleic acid wherein the nucleic acid comprises a sequence that cleaves RNA. Single-stranded nucleic acids can fold into tertiary structures and act as catalysis similar to enzymes made of protein. Ribozymes, RNAzymes, and deoxyribozymes, DNAzymes, have been isolated from naturally occurring molecules and optimized from random-sequence populations using in vitro selection. A combinatorial strategy may be used to create numerous classes of nucleic acid-cleaving DNAzymes and RNAzymes. DNAzymes and RNAzymes often, but not exclusively, catalyze cleavage of the RNA 3',5'-phosphodiester linkage by promoting an internal transesterification reaction to produce 2',3'-cyclic phosphate and 5'-hydroxyl termini.

In certain embodiments, the disclosure relates to particles conjugated to a cleaving nucleic acid such as DNAzyme 10-23. The DNAzyme 10-23 is comprised of a sequence of DNA that will cleave mRNA strands that contain an unpaired purine-pyrimidine pair. The DNAzyme 10-23 is typically flanked by a recognition sequence that will specifically recognize a short region of the target mRNA. Therefore, the DNAzyme will recognize the complementary mRNA, hybridize, and cleave at a site. In certain embodiments, this disclosure contemplates that the cleaving nucleic acids comprise sequences of DNAzymes 8-17 and 10-23. Santoro & Joyce disclosed a general purpose RNA-cleaving DNAzymes 8-17 and 10-23. See PNSA, 1997, 94 (9), 4262-4266, hereby incorporated by reference.

In certain embodiments, this disclosure contemplates that the cleaving nucleic acids comprise 8-imidazolyl modified deoxy adenosines RNaseA mimicking DNAzymes. Perrin et al., disclose modified DNAzymes 20-49 containing amine, guanidine, and imidazole-modified dNTPs. Org Biomol Chem 2011, 9 (7), 2266-2273, hereby incorporated by reference.

In certain embodiments, this disclosure contemplates that a cleaving nucleic acid is DNAzyme 10-23 catalytic core; DNAzyme 8-17 catalytic core, 5'-TCCGAGCCGGACGA (SEQ ID NO: 24); Dz16.22-11 catalytic core, 5'-GTGACCCCUUG (SEQ ID NO: 25); Dz9-86 catalytic core, 5'-UCAUGCAGCGCGUAGUGUC (SEQ ID NO: 26); or Dz12-91 catalytic core UGAUGCAGCGCAUGU-GUC (SEQ ID NO: 27); or FR17_6 catalytic core, AAGCAGUUAAGAC (SEQ ID NO: 28).

Metal Particles, Coatings, and Preparation

This disclosure relates to particles conjugated to a cleaving nucleic acid wherein the nucleic acid comprises a sequence that cleaves RNA, e.g., DNAzyme or RNAzyme. In certain embodiments, the particle comprises or consists essentially of a metal such as gold, silver, copper, iron, or iron oxide. Typically, the particle is a metal nanoparticle. In some embodiments, the cleaving nucleic acid is conjugated to the metal particle through surface coated polymer.

Contemplated particles include pegylated colloidal gold and iron oxide nanoparticles. See Qian et al., Nature Biotechnology, 2008, 26, 83-90, Hadjipanayis et al., Cancer Research, 2010, 70(15):6303-6312, and Peng et al., Int J Nanomedicine, 2008, 3(3): 311-321, all hereby incorporated by reference. A couple of approaches may be used for the chemical synthesis of contemplated gold nanoparticles. Alkanethiols may be used to stabilize gold particles. See, e.g., Brust et al., J Chem Soc, Chem Commun, 1994, 801-02 and Templeton et al., Acc Chem Res, 2000, 33, 27, all hereby incorporated by reference. In another approach, one uses sodium citrate as a reducing agent and stabilizing ligand. See Turkevich et al., Discuss Faraday Soc, 1951, 11, 55, hereby incorporated by reference. The particle size can be controlled by the gold precursor/citrate molar ratio. Kairdolf & Nie disclose the production of multidentate-protected colloidal gold nanoparticles. See J. Am. Chem. Soc. 2011, 133, 7268-7271, hereby incorporated by reference.

Nanoparticles are typically prepared with a mean particle diameter of 4-100 nm. Iron-oxide nanoparticles (IONPs) may be prepared by aging a stoichiometric mixture of ferrous and ferric salts in aqueous media under basic conditions. Control over particle size (2-20 nm) and shape is provided by adjusting the pH, ionic strength and the concentration of the growth solution. The nanoparticles can be functionalized in situ using additives such as organic compounds (e.g. sodium citric) or polymers (e.g. dextran, polyvinyl alcohol). Other metals such as gold, cobalt, nickel, and manganese may be incorporated into the material.

High-temperature decomposition of $Fe(CO)_5$ in organic solvents is another way to prepare IONPs. Size (3-19 nm) can be varied using alternative temperatures. Flame spray pyrolysis yields a range of magnetite, maghemite and wustite (FeO) particles IONPs. Iron precursor such as $Fe(CO)_5$ and $Fe(NO_3)_3$ may be used. Flame spray pyrolysis can be used to produce different nanoparticles ($TiO_2$, $ZrO_2$, silica, etc.) as well as hybrid particles (e.g. silica-IONPs).

Hydroxyl groups on the IONP provide a place for synthetic attachment of different functional groups. A range of chemistries can be used to stabilize metal nanoparticles, exploiting electrostatic, hydrophobic, chelating and covalent interactions. Carboxylic acid groups can interact with the surface of IONPs by coordination processes. Typically, IONP synthesis in organic solvents is conducted in oleic acid. A polymer coating on the IONPs is preferred. Polymer attachment to the IONP surface by an initiator fixed to the surface of the IONPs and the polymer is grown from the surface. Alternatively, a functional, pre-formed polymer is grafted onto IONPs in situ. Copolymers with hydrophobic groups, carboxylic acid groups, polyethylene glycols, or amine groups are contemplated Conjugating cleaving nucleic acids to the polymers can be accomplished using a variety of methods. For example, a primary amine containing nucleic acid may be conjugated to the carboxylic acid groups on a coated polymer mediated by a coupling reagent such as EDAC. See, e.g., Yang et al., Small, 2009, 5(2):235-43, hereby incorporated by reference. Other coupling methods are contemplated, e.g., the avidin/streptavidin-biotin interactions may be used, e.g., streptavidin may be coupled to the coated polymer surface and biotin may be linked to the cleaving nucleic acid.

Nanozyme RNA Splicing

Tools that can manipulate nucleic acids are very powerful, capable of controlling cellular outcomes. RNA in particular is a desirable and accessible target, as it is in the cytoplasm, not bound by histones and chromatin, and is thus more accessible than DNA. Modulating RNA can have tremendous potential for elucidating RNA biology, gene knockdown, and regulating splicing. Two major methods have been developed to manipulate RNA. The first operates by modulating the activity of the spliceosome, while the second approach employs RNA modifying enzymes and ribozymes. Key examples of the latter approach include adenosine deaminase and the tRNA endonuclease from Methanococcus jannaschii (MJ-EndA). Adenosine deaminases that act on RNA (ADAR) have been shown to create A to G point mutations by converting adenosine to inosine, which can be used to correct RNA errors. For example, by coupling to an antisense RNA strand and a gamma-phage RNA binding protein, it can target and correct nonsense mutations in the cystic fibrosis conductance regulator, restoring translation at 100% efficiency. Alternatively, MJ-EndA functions by cleaving bulge-helix-bulge (BHB) regions in RNA. Artificial BHBs can be created in trans by introducing a guide RNA strand that recruits MJ-EndA to these RNA sequences. The cleavage product is then repaired by cellular ligases. MJ-EndA has demonstrated activity for splicing in vitro. This approach requires delivery of a plasmid encoding the endonuclease, along with the guide RNA strand, and has shown an efficiency as high as 30% splicing.

In addition to protein enzymes, ribozymes or catalytic RNAs, are actively used to control RNA splicing. Originally discovered as self-slicing group I introns, ribozymes have been modified and used for RNA knockdown, intro removal, as well as trans-splicing of 3' and 5' segments. Thus far ribozyme-based editing has shown 10-50% efficiency in mammalian cells under ideal conditions. Given the importance of manipulating RNA in cell and molecular biology and biochemistry, the development of new approaches to modify RNA is highly desirable.

This disclosure contemplates a method for RNA splicing by generating a particle comprising RNA cleaving and ligating enzymes onto a nanoparticle (NP or AuNP) scaffold. In certain embodiments, 10-23 DNAzyme catalytic core is used as the site-specific RNA-cleaving component of the nanozyme. In certain embodiments, the 10-23 DNAzyme is composed of a Mg/Mn$^{2+}$ dependent 15-nucleotide (nt) catalytic core of sequence GGCTAGCTACAACGA (SEQ ID NO: 2) flanked by two 6-10 nt binding arms which can be tuned to bind any RNA target with high specificity. In certain embodiments, two unique site-specific cleaving DNAzymes are used together.

In certain embodiments, the sequence of DNAzyme 1 (Dz$_1$) is GTTTCTCTAGGCTAGCTA-CAACGAGTGTTCTTG (SEQ ID NO: 6) or TTTCTCTAGGCTAGCTACAACGAGTGTTCTT (SEQ ID NO: 18). In certain embodiments, the sequence of DNAzyme 2 (Dz2) is TGCTCTCCAGGCTAGCTA-CAACGACCTGCACCT (SEQ ID NO: 8) or GCTCTCCAGGCTAGCTACAACGACCTGCACC (SEQ ID NO: 19).

The DNAzymes are joined by their 3' ends to the gold nanoparticle. In certain embodiments, the sequence of Dz$_1$ attached to the particle is GTTTCTCTAGGCTAGCTA-CAACGAGTGTTCTTGTTTTTTTTTT/3ThioMC3-D/ (SEQ ID NO: 20). In certain embodiments, the sequence of Dz$_2$ attached to the particle is TGCTCTCCAGGCTAGC-TACAACGACCTGCACCTTTTTTTTTTT/3ThioMC3-D/ (SEQ ID NO: 21). In other embodiments, the DNAzymes can be designed to target specific alternative sequences.

DNAzyme cleaves at purine/pyrimidine junctions—most often UA or GU residues after which the binding arms dissociate as they are no longer thermally stable, allowing for a new round of binding and cleavage to take place. In certain embodiments, mammalian cells readily internalize DNAzyme-AuNP conjugates. In certain embodiments, DNAzyme-AuNP conjugates are used for gene knockdown in vitro and in vivo. DNAzymes are synthetic constructs generated through rounds of selection (SELEX) for a RNA cleavage activity.

In certain embodiments, RNA 2',3'-Cyclic Phosphate And 5'-OH Ligase (RtcB) is used as the RNA ligating enzyme of the nanozyme. RtcB can directly ligate the termini produced by DNAzymes: 2'3'-cyclic phosphate and 5'-OH. RtcB is conserved throughout bacteria, archea and metazoan, having functions in bacteria for RNA repair, and in metazoan, for splicing of tRNAs and upregulating the unfolded protein response. RtcB's natural substrate for ligation is hydrolysed stem-loop RNA.

In certain embodiments, this nanozyme provides a delivery vehicle into cells. In certain embodiments, the nanozyme sequesters its enzyme cargo onto the AuNP surface, away from degrading proteases and nucleases, increasing stability over current strategies. The spliced product is not a substrate for the DNAzymes, helping to move the reaction towards completion.

In certain embodiments, this technology is used for splicing RNA in vitro. In other embodiments, this technology is used for splicing RNA in vivo.

EXPERIMENTAL

Rtcb is More Active on Stem-Loops than Linear RNA

To test the activity of RtcB, the ligase was isolated using a LacI inducible plasmid expressing Escherichia coli n-terminal hexahistidine-tagged RtcB. Bold are codons for the hexahistidine-tag followed by the two cysteine residues.

```
DNA sequence encoding E. coli RtcB-Cys (Accession
#P46850)
                                     (SEQ ID NO: 22)
5'-ATGCACCATCATCATCACCATTGTTGCGGTAATTACGAATTACTGACC

ACTGAAAATGCCCCGGTAAAAATGTGGACCAAAGGCGTGCCGGTAGAGGCC

GATGCGCGTCAGCAACTTATTAATACGGCGAAGATGCCGTTTATTTTCAAA

CATATTGCGGTAATGCCTGATGTACACCTGGGTAAAGGTTCCACCATTGGT

AGCGTGATCCCGACCAAAGGGGCGATTATTCCGGCGGCGGTGGGCGTGGAT

ATTGGCTGTGGAATGAACGCGCTGCGTACCGCGTTAACGGCGGAAGACCTG

CCTGAAAACCTGGCAGAGCTGCGTCAGGCGATTGAAACGGCCGTGCCGCAC

GGGCGTACCACTGGCCGTTGTAAACGTGATAAAGGTGCCTGGGAAAATCCA

CCTGTTAACGTCGATGCTAAATGGGCTGAGCTTGAAGCCGGTTATCAGTGG

TTAACGCAAAAATATCCCCGTTTCCTGAATACCAATAACTATAAACACCTG

GGAACGCTGGGAACCGGTAACCACTTTATTGAAATCTGCCTTGATGAGTCG

GACCAGGTGTGGATTATGCTGCACTCCGGTTCACGCGGAATTGGTAACGCC

ATCGGGACTTACTTTATCGATCTGGCACAAAAAGAGATGCAGGAAACGCTT

GAGACGTTGCCGTCGCGTGATCTGGCGTACTTTATGGAAGGTACGGAATAC

TTTGATGATTACCTGAAAGCCGTGGCCTGGGCGCAGCTTTTTGCCAGCCTT

AACGCGATGCGATGATGGAAAACGTGGTAACGGCATTGCAGAGCATTACG

CAGAAAACGGTCAGACAGCCACAAACGCTGGCGATGGAAGAGATCAACTGT

CACCACAACTATGTGCAAAAAGAACAGCACTTTGGTGAAGAGATCTACGTG

ACGCGTAAAGGCGCGGTGTCTGCGCGTGCTGGTCAATATGGAATTATTCCC

GGTTCGATGGGAGCAAAAAGCTTTATCGTCCGTGGGCTGGGAAATGAAGAG

TCGTTCTGTTCGTGCAGCCACGGTGCCGGGCGGGTAATGAGCCGAACTAAA

GCGAAAAAACTGTTCAGCGTGGAAGATCAAATTCGTGCCACCGCGCATGTG

GAATGCCGTAAAGATGCCGAAGTGATCGACGAAATCCCGATGGCGTATAAA
```

-continued

```
GATATTGATGCGGTGATGGCGGCACAAAGCGATCTGGTGGAAGTTATCTAT

ACCCTGCGTCAGGTGGTGTGCGTAAAAGGATAA-3'
```

Amino acid sequence of E. coli RtcB-Cys
(SEQ ID NO: 23)

```
MHHHHHHCCGNYELLTTENAPVKMWTKGVPVEADARQQLINTAKMPFIFKH

IAVMPDVHLGKGSTIGSVIPTKGAIIPAAVGVDIGCGMNALRTALTAEDLP

ENLAELRQAIETAVPHGRTTGRCKRDKGAWENPPVNVDAKWAELEAGYQWL

TQKYPRFLNTNNYKHLGTLGTGNHFIEICLDESDQVWIMLHSGSRGIGNAI

GTYFIDLAQKEMQETLETLPSRDLAYFMEGTEYFDDYLKAVAWAQLFASLN

RDAMMENVVTALQSITQKTVRQPQTLAMEEINCHENYVQKEQHFGEEIYVT

RKGAVSARAGQYGIIPGSMGAKSFIVRGLGNEESFCSCSHGAGRVMSRTKA

KKLFSVEDQIRATAHVECRKDAEVIDEIPMAYKDIDAVMAAQSDLVEVIYT

LRQVVCVKG.
```

RtcB activity was assayed using fluorescein-labeled target RNAs (fluorescein amidite-FAM), and the products were quantified using 15% polyacrylamide gel electrophoresis (PAGE). Action of RtcB was tested using a 7-mer stem—loop tRNA$^{glu}$ mimic and found that RtcB ligated this substrate with 100% efficiency, while it ligated two 10-mer linear RNA strands with an efficiency of up to 46%. Additionally, the stem—loop target ligation was rapid, reaching completion within 2 min. RtcB is more active on stem—loops than on linear RNA, suggesting that it will also be the preferred substrate for splicing reactions.

Figure 2A:
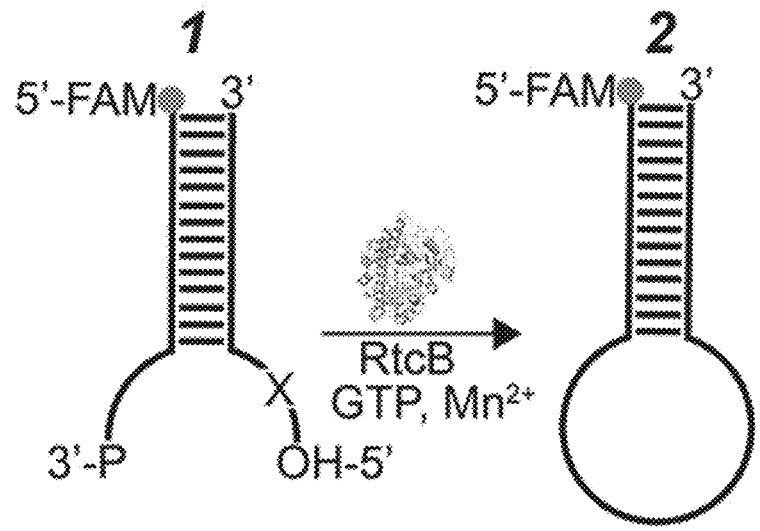
FIG. 2A illustrates testing the role of loop size in ligation efficiency including a schematic showing model RNA substrate for testing RtcB activity as a function of loop size. "X" indicates added nucleotides.
Figure 2B:
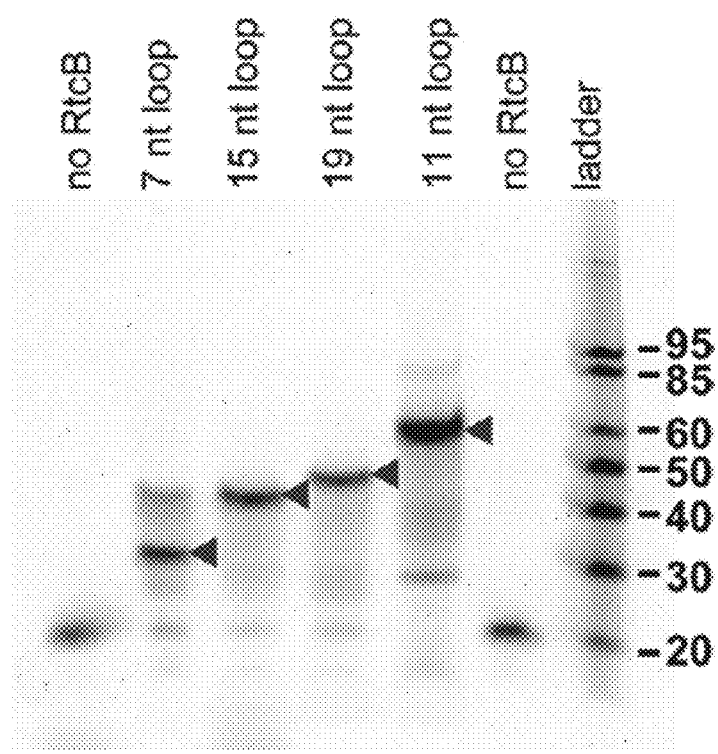
FIG. 2B shows data where a reaction was conducted at 37° C. for 1 hr, 200 nM FAM-labeled strand, 250 nM unlabeled strand, 150 mM NaCl, 1 mM $Mn^{2+}$, 0.1 mM GTP and 1 μM RtcB. Lane 1: 19 nt FAM-labeled strand alone; lane 6, stem-loop of 7 nt without RtcB to ligate. Arrows indicate ligation products. Note that RtcB can ligate either 2'3'-cyclic phosphates or 3' phosphates.
Figure 3A:
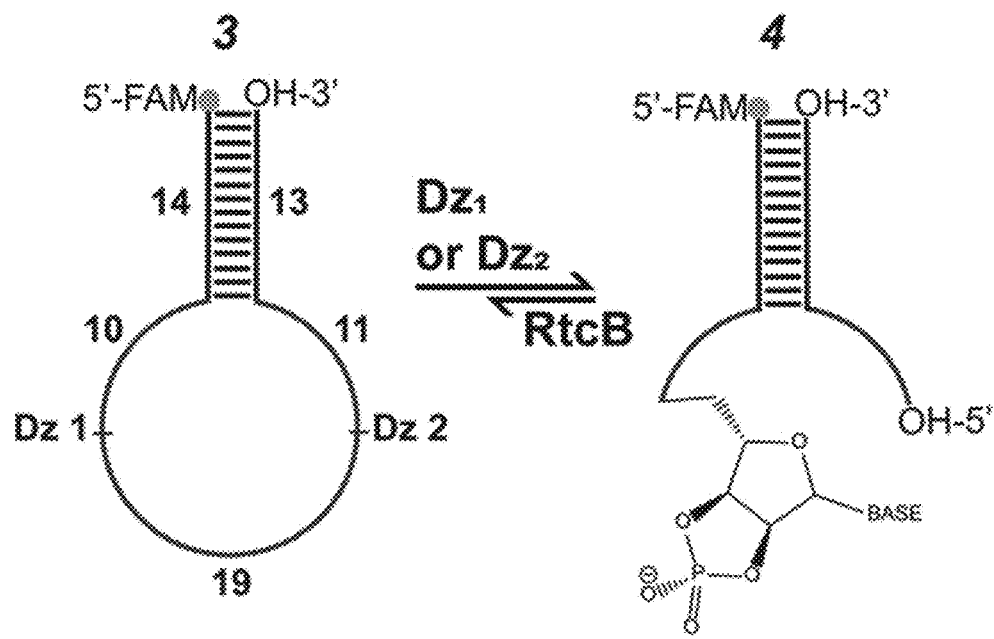
FIG. 3A is a schematic showing DNAzyme cleavage and ligation back to substrate 3 (FIG. 1E). RNA is shown in light and DNA in black.
Figure 3B:
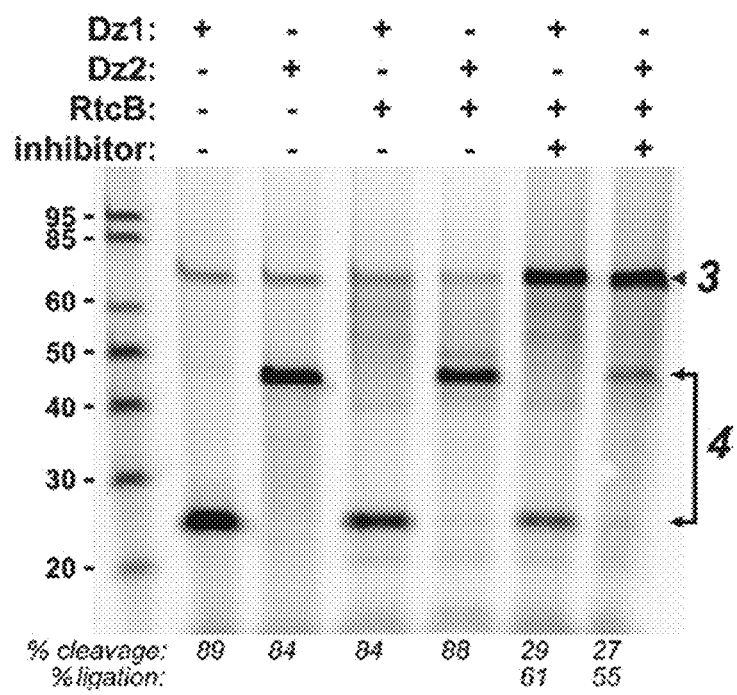
FIG. 3B is a gel indicating single cleavage reactions and ligation back to substrate. Lanes 2-3: single Dz digests; lanes 4-5: single Dz digests after RtcB addition; lanes 6-7: same reaction shown in lanes 4-5 after addition of inhibitor strands complementary to the Dz(s). Ligation reactions contain 150 mM NaCl, 2 mM $Mn^{2+}$, 0.4 μM substrate 3, 0.4 μM $Dz_1$ or $Dz_2$, 0.42 μM Dz inhibitor (lane 6-7), 0.4 mM GTP and 2.2 μM RtcB. Arrow indicates ligation product. Note that lanes were loaded evenly.

The efficiency of RtcB ligation was examined as a function of stem—loop size (7, 11, 15, and 19 nts), to determine if RtcB could ligate stem—loops larger than tRNA anticodon loops. The tRNA$^{glu}$ stem—loop were modified with increasing numbers of unpaired base pairs and introduced additional unpaired nucleotides on the 5'-end (FIG. 2A), increasing loop size. The stem—loops tested were ligated to near 100% efficiency (FIG. 2B). To interrogate the ligation of loops larger than 19 nts, DNAzymes (Dz$_1$ and Dz$_2$), a DNA/RNA hybrid stem—loop target was used (FIG. 3A, 3), producing single-stranded overhangs of 10 and 30 nts or 11 and 29 nts, with a total loop size of 40 nts. After DNAzyme cleavage of the RNA/DNA hybrid substrate for 2 h, an aliquot of the reactions was taken (FIG. 3B, lines 2-3) and an inhibitor strand complementary to the DNAzymes was introduced along with RtcB. The reaction was then allowed to proceed for another 1 h (FIG. 3B, lanes 6-7). Using PAGE, the efficiency of RtcB ligation of these cleavage products was assessed with and without inhibitor strands. Analysis of the resulting gel showed that when an inhibitor strand was present, these step—loops were ligated back to substrate 3 with 55-60% efficiency (FIG. 3B, lanes 6-7). The inhibitor strands inactivate the DNAzymes blocking DNAzyme action and allowing for RtcB ligation. The reduction in efficiency is likely due to the enlarged loop, as well as the limited cyclic phosphodiesterase activity of RtcB. RtcB is amenable for ligation of stem—loops as large as 40 nts and shows that it can process the products of DNAzyme cleavage.

DNAzymes and RtcB Splice an RNA Stem—Loop

Figure 4A:
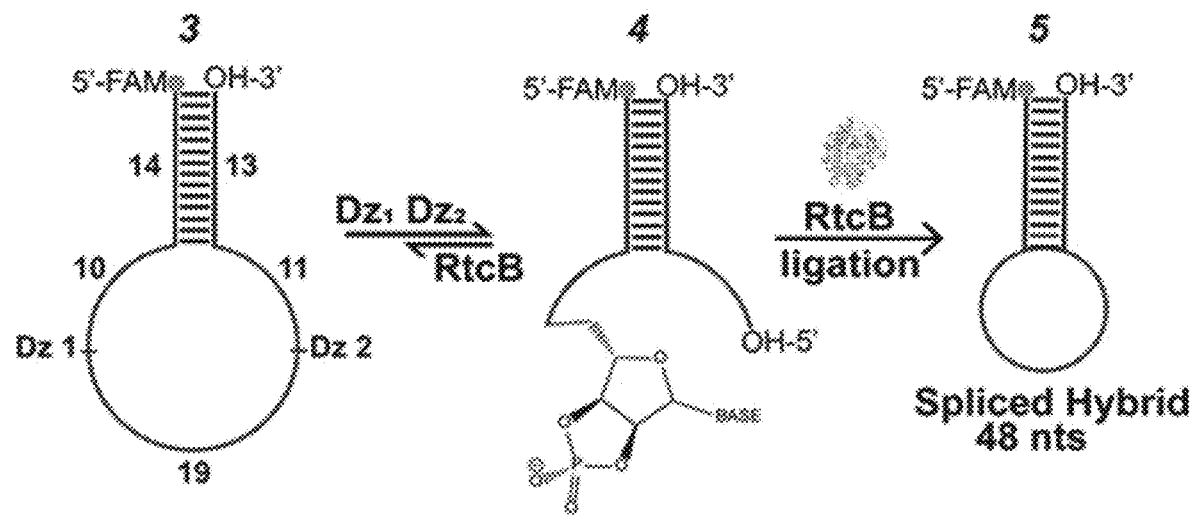
FIG. 4A illustrates RtcB ligation of DNAzyme cleavage products and splicing including a schematic showing reactions used to test splicing. 5'-FAM-labeled in vitro splice substrate 3 is cleaved, removing 19 nt intron to produce 4. RtcB addition produces spliced stem-loop 5.
Figure 4B:
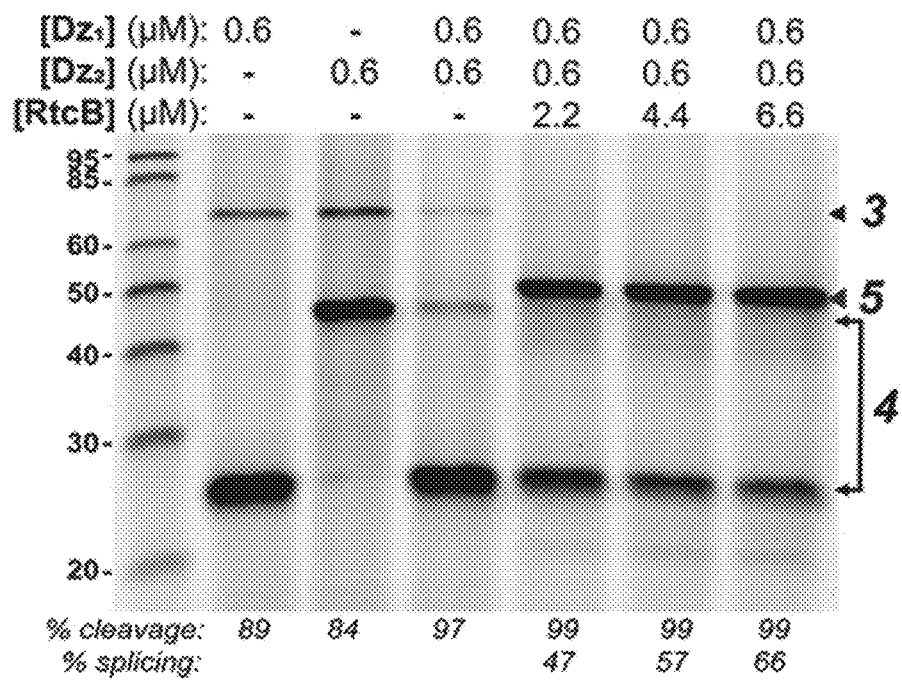
FIG. 4B shows cleavage and splice reaction with soluble Dz(s) and RtcB. $Dz_1$ (lane 2) and $Dz_2$ (lane 3) single cleavage produces bands at 24 and 43 nts. Addition of RtcB to a $Dz_1$ $Dz_2$ double digest produces splice product (arrow). Reaction conditions: 150 mM NaCl, 0.6 μM each Dz, 0.6 μM substrate 3, 2 mM $Mn^{2+}$, 0.4 mM GTP, 2.2, 4.4 or 6.6 μM RtcB. DNAzyme cleavage (2 hrs) and RtcB ligation (1 hr) proceeded at 37° C.

Experiments were performed to determine whether it was possible for DNAzymes and RtcB to splice in a one-pot reaction. Substrate 3 was incubated with an equimolar concentration (0.6 μM) of both Dz$_1$ and Dz$_2$ for 2 h in the presence of 2 mM Mn$^{2+}$. The DNAzymes bound adjacent sites in the loop region of the step—loop substrate 3 and cleaved, removing a 19 nt intron (FIG. 4A, 4). After cleavage, RtcB was added to the reaction at different concentrations (2.2, 4.4, and 6.6 μM). Upon addition of RtcB, a smaller spliced step—loop product 5 was produced (48 nts) at 47-66% yield, depending on the concentration of the enzyme (FIG. 4B). In general, splicing yield varied between 45% and 68% with 2.2 μM of RtcB. Yield was calculated by integrating the splice product band intensity and dividing by the integrated intensity of all the bands per lane. All values were background subtracted using the integrated intensity above and below each band. Note that in this case, a hybrid RNA/DNA substrate was used for splicing; however, all RNA substrates may also be used. Interestingly, RtcB and DNAzymes spliced RNA targets both in sequential reactions (with DNAzyme addition followed by RtcB addition) and in one-pot reactions, with similar yields. As with the ligation of RNA step—loops, the splice reaction is also relatively fast, and splice product was observed 5 min after addition of RtcB enzyme.

There are two possible reasons that likely limit splice yield. The first is that the DNAzymes could be binding to the target and not dissociating adequately, thus inhibiting RtcB binding and ligation. Additionally, stalled or inactive RtcB enzyme may sequester RNA ends, binding them but not effectively performing the ligation reaction. Experiments were performed to test whether DNAzymes could be inhibiting the splice reaction. DNAzymes were bound with a complementary strand after cleavage. RtcB was added. The yield of this reaction showed a 5% increase over reactions with free DNAzymes. DNAzyme arms were shortened from 9 nts to 8 and 7 nts, to decrease the Tm, reducing DNAzyme—target stability and enhancing product dissociation. A 12% increase in splicing (from 48% to 60%) was observed upon using 8 nt arms over 9 nt arms. However, no additional improvement in splicing was observed for the 7 nt arm DNAzyme. Only Dz$_2$ was tested with 7 nt arms, since Dz$_1$'s Tm was already significantly reduced with 8 nt arms, and further shortening the arms would likely limit binding to the target.

DNAzyme arms alter splicing rates, but that factor alone cannot account for the observed lower yield. Interestingly, ligation efficiency was nearly quantitative when 3'-P termini were used for the step—loop ligation, suggesting that the 2',3'-cyclic phosphates formed as the DNAzyme cleavage products reduce the yield of splicing. As RtcB first converts the 2',3'-cyclic phosphate to a 3'-P before ligation, it is possible the cyclic phosphatase reaction stalls splicing yield. Nevertheless, these splice reactions show that DNAzymes and RtcB are indeed able to function under identical conditions to splice RNA step—loop targets, removing a 19 nt intron. These results confirm the potential for a splicing nanozyme system employing both classes of enzymes.

Dz$_1$Dz$_2$NP Splicing Using Excess RtcB

Figure 5A:
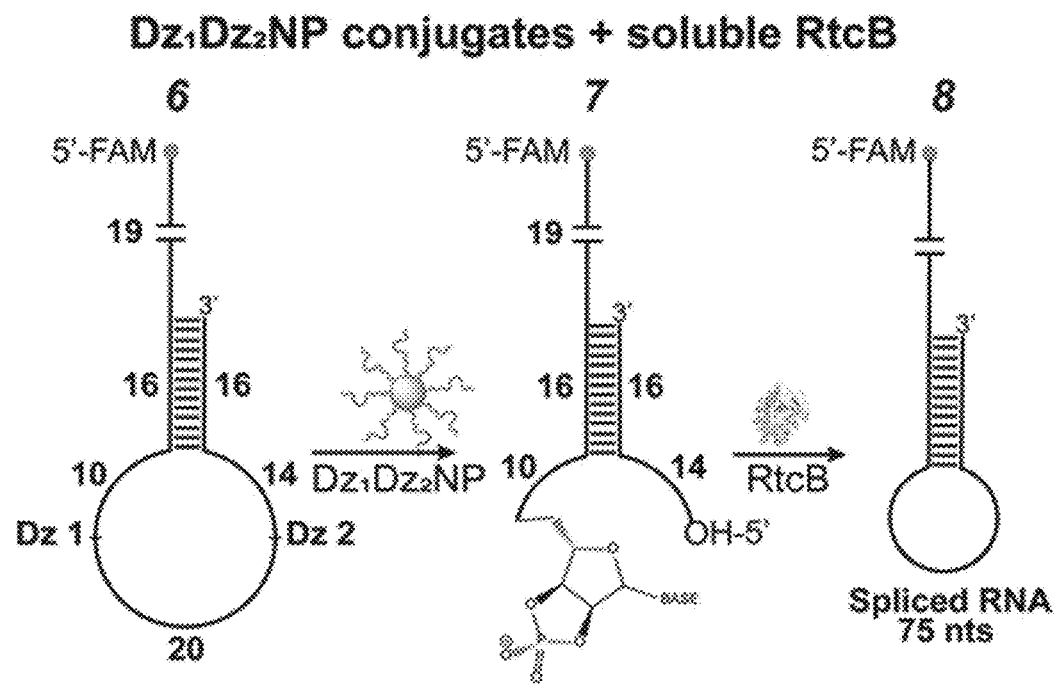
FIG. 5A illustrates DNAzyme conjugates ($Dz_1Dz_2NPs$) can splice with excess soluble RtcB including a scheme showing splicing by $Dz_1Dz_2NPs$ and RtcB on RNA substrate.
Figure 5B:
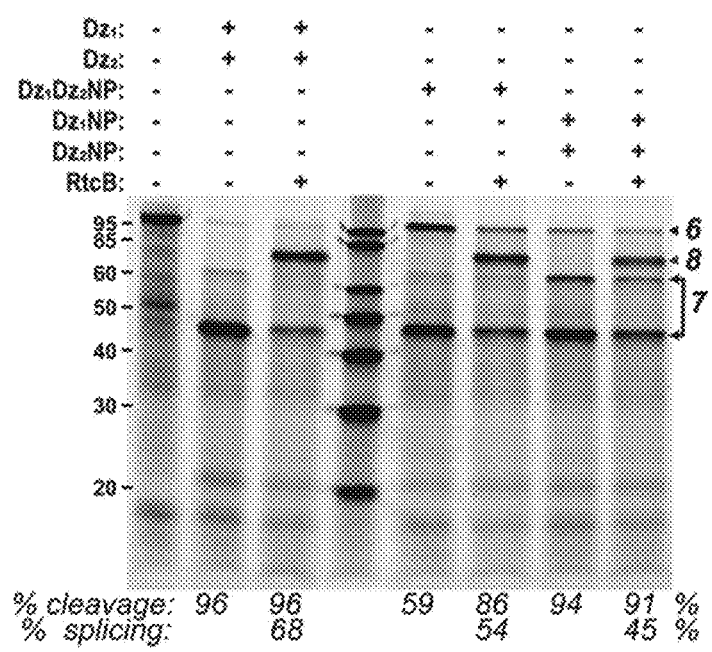
FIG. 5B shows data where splicing by soluble DNAzymes is compared to NPs with either, both or single, Dz's attached. Arrow indicates splice product. Reaction conditions: 150 mM NaCl, 1 mM $Mn^{2+}$, 0.4 μM substrate 6, 0.4 mM GTP, 2.2 μM RtcB, lanes 2-3, 0.4 μM Dz(s), lanes 5-6, 9 nM $Dz_1Dz_2NPs$, lanes 7-8, 9 nM $Dz_1NP$ and $Dz_2NP$. Cleavage was conducted at 37° C. for 2 hrs and splicing at 37° C. for 1 hr. Note that the cleavage yield increased in lane 6 compared to lane 5 likely due to the additional 1 hr incubation time following treatment with RtcB.

As a first step toward splicing with a nanozyme composed of both DNAzymes and RtcB conjugated to a gold nanoparticle scaffold, it was first tested whether soluble RtcB could splice in the presence of DNAzyme-functionalized gold nanoparticle conjugates (Dz$_1$Dz$_2$NPs). To produce Dz$_1$Dz$_2$NPs, thiolated DNA was incubated with citrate stabilized AuNPs and progressively salted. After washing to remove excess salt, mature Dz$_1$Dz$_2$NPs were then incubated with an RNA substrate (FIG. 5A, 6), allowing cleavage to proceed. Dz$_1$Dz$_2$NPs cleaved target RNA producing 7 with an efficiency between 86% and 94%, in the presence of 1 mM Mn$^{2+}$. When RtcB was added to these digests, a 54% splicing yield was observed, similar to what was obtained for splicing with soluble DNAzymes and RtcB. Additionally, mixing $Dz_1NPs$ and $Dz_2NPs$ also resulted in efficient cleavage. These products were spliced at a yield of 45% (FIG. 5B, lanes 7-8). The yield was lower in this case possibly due to the added steric bulk of two AuNPs being involved in the cleavage reaction. For single component DzNPs, the number of Dzs per NP was quantified using a fluorescence assay, which showed that there were 102±9 strands of $Dz_1$ and 54±6 strands of $Dz_2$ on the AuNPs. Since for $Dz_1Dz_2NPs$, each Dz was added in equimolar amounts, the number of strands of each on the NP may be estimated at half their number on single component DzNPs. Overall, these experiments show that splicing is effectively achieved with DNAzyme—nanoparticle conjugates and excess soluble RtcB.

Nanozyme Synthesis

Figure 6A:
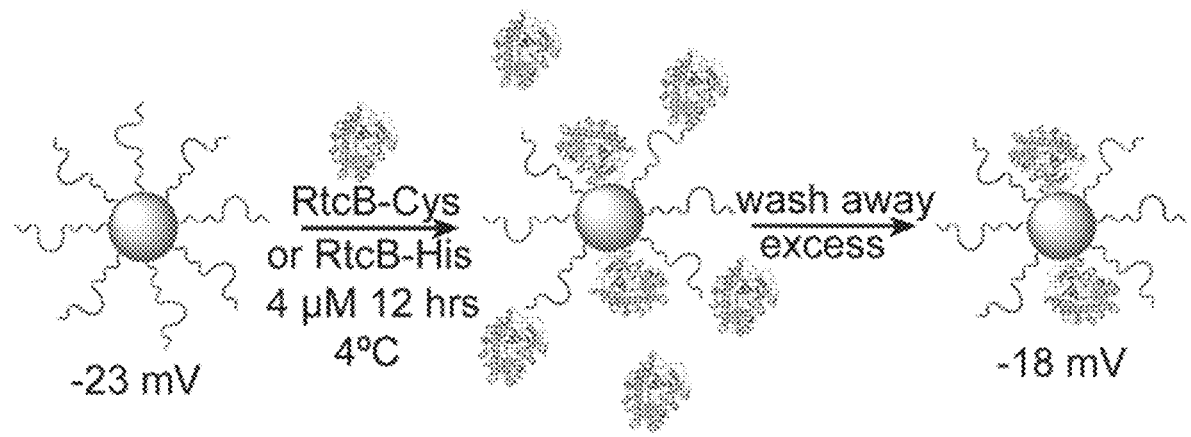
FIG. 6A shows a scheme illustrating nanozyme synthesis. Zeta potential=−22.5±1.5 for $Dz_1Dz_2NPs$ and −17.7±1.4 for nanozymes in 10 mM Tris-HCl, pH 7.4.
Figure 6B:
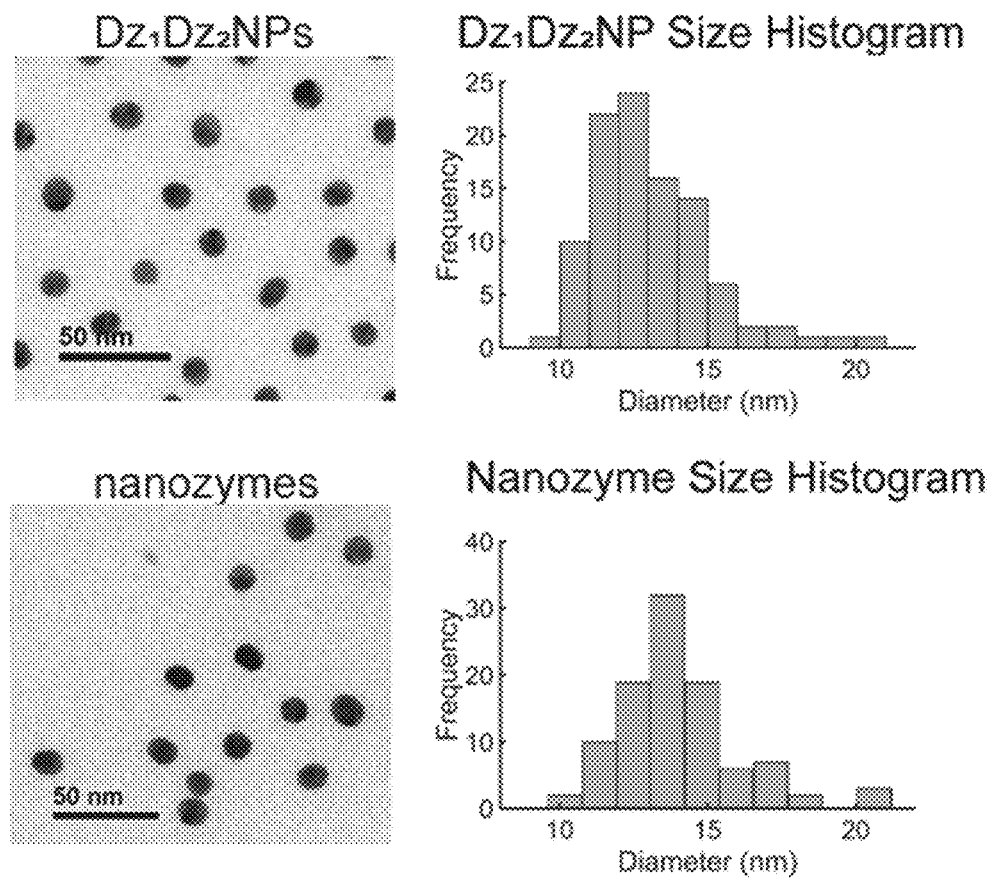
FIG. 6B shows transmission electron microscope (TEM) characterization of $Dz_1Dz_2NPs$ and nanozymes. DNAzymes and RtcB are not visible in unstained TEM; however, no aggregation was observed.
Figure 6C:
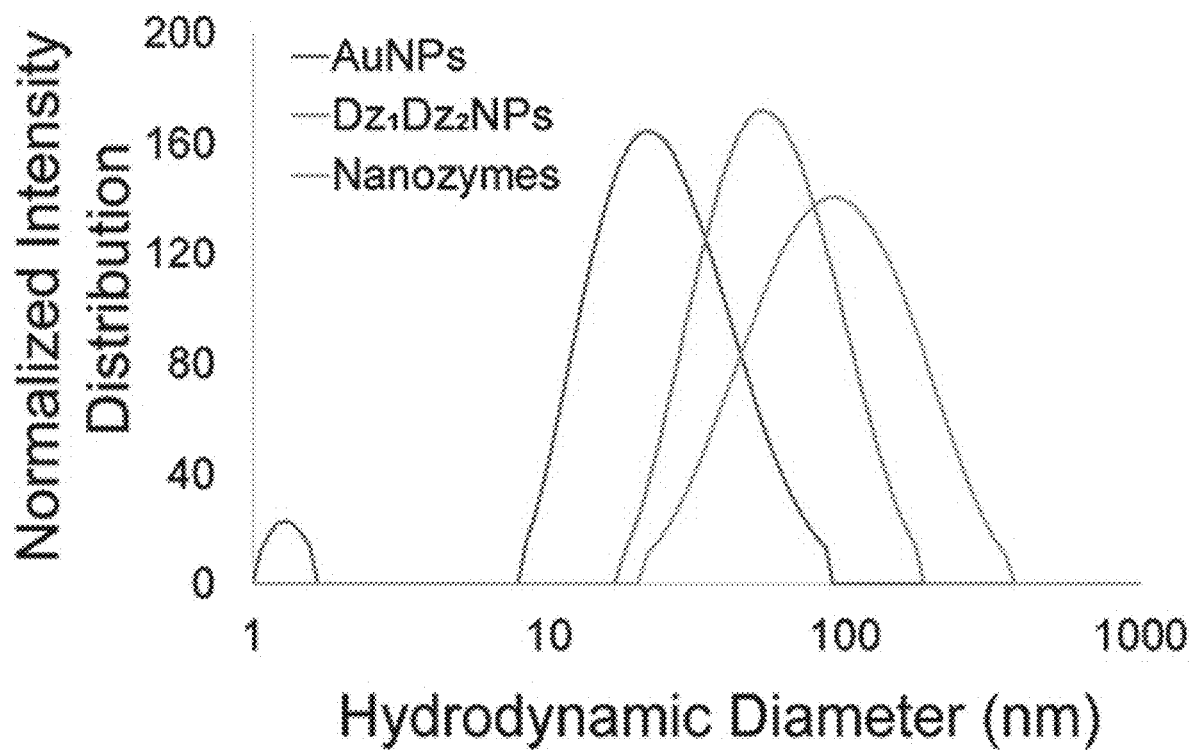
FIG. 6C shows data on DLS of unmodified AuNPs, $Dz_1Dz_2NPs$ and nanozymes.
Figure 6D:
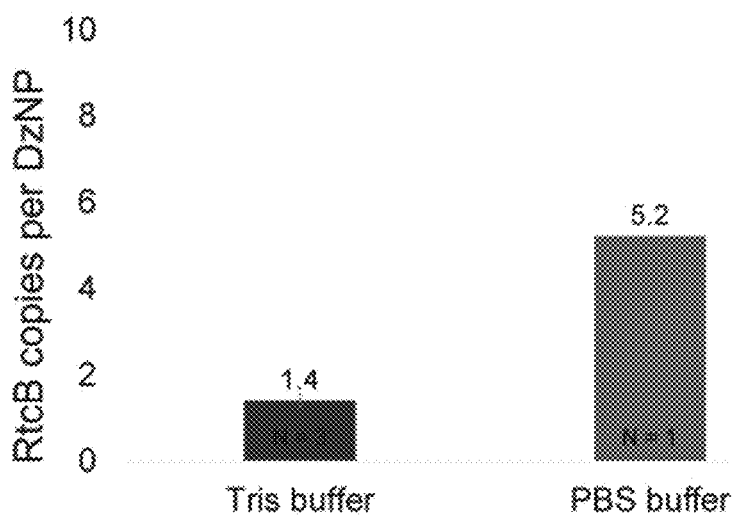
FIG. 6D is a plot showing the measured density of RtcB on nanozymes. Measurement was performed using fluorescence spectrometry.
Figure 6E:
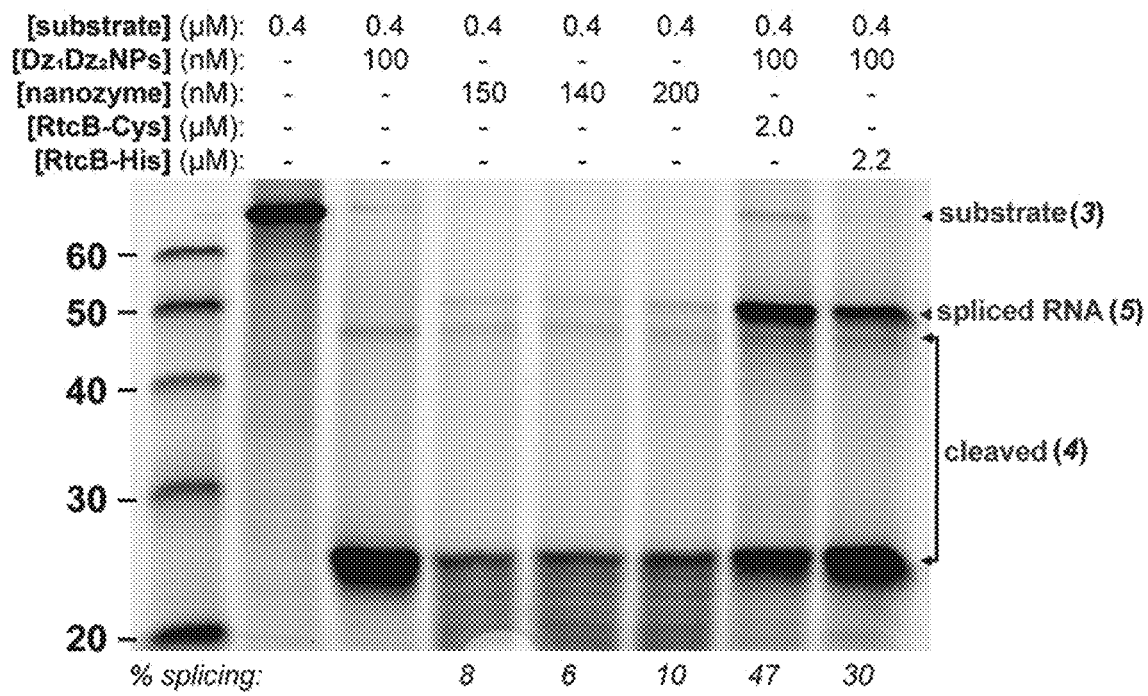
FIG. 6E shows data on triplicate nanozyme splicing reactions. Lane 2: RNA/DNA hybrid substrate 3 only; lane 3: Negative control containing $Dz_1Dz_2NPs$ and no RtcB; lane 4-6: nanozymes after washing 3 times yields splice product (arrow); lane 7: positive control with $Dz_1Dz_2NPs$ and 2 μM soluble RtcB-Cys; lane 8: positive control with $Dz_1Dz_2NPs$ and 2.2 μM soluble RtcB-His. Reaction conditions: 0.4 μM substrate, 150 mM NaCl, 0.4 mM GTP, 2 mM $Mn^{3+}$, 37° C. for 2 hrs.

To produce complete nanozymes, both DNAzymes and RtcB were attached to a single particle. The RtcB enzyme was engineered with two cysteine residues at the N-terminus to enhance AuNP binding through thiol—Au chemistry. $Dz_1Dz_2NPs$ were synthesized. Afterward, RtcB-Cys (4.7 µM) was attached to these $Dz_1Dz_2NPs$ in an overnight incubation at 4° C. in 100 mM Tris-HCl, thus allowing RtcB binding by thiol exchange and production of nanoparticles. The zeta potential of the $Dz_1Dz_2NPs$ and nanozymes was also measured (FIG. 6A). These measurements suggest that RtcB alters the zeta potential of the $Dz_1Dz_2NP$ particles. A fluorescence assay indicated that an average of 1.4 RtcB molecules were bound to each $Dz_1Dz_2NP$. However, when the thiol exchange was performed in the presence of 1×PBS, 5.2 RtcB were bound per $Dz_1Dz_2NP$. This greater degree of binding is likely due to charge screening, as 1×PBS has a greater ionic strength than the Tris buffer used for binding studies. The cysteine residues were important in the binding of the RtcB to the AuNPs to produce complete nanozymes, since His-tagged RtcB failed to bind to AuNPs, as shown by failure to generate splice product after washing the particles. The AuNPs, $Dz_1Dz_2NPs$, and nanozymes were characterized by transmission electron microscopy (TEM) and dynamic light scattering (DLS) (FIG. 6B and FIG. 6C). TEM shows that the $Dz_1Dz_2NPs$ and nanozymes were not aggregated by addition of DNA and protein to the surface of the gold.

Nanozyme Conjugates Splice RNA Stem—Loop Targets

Figure 6F:
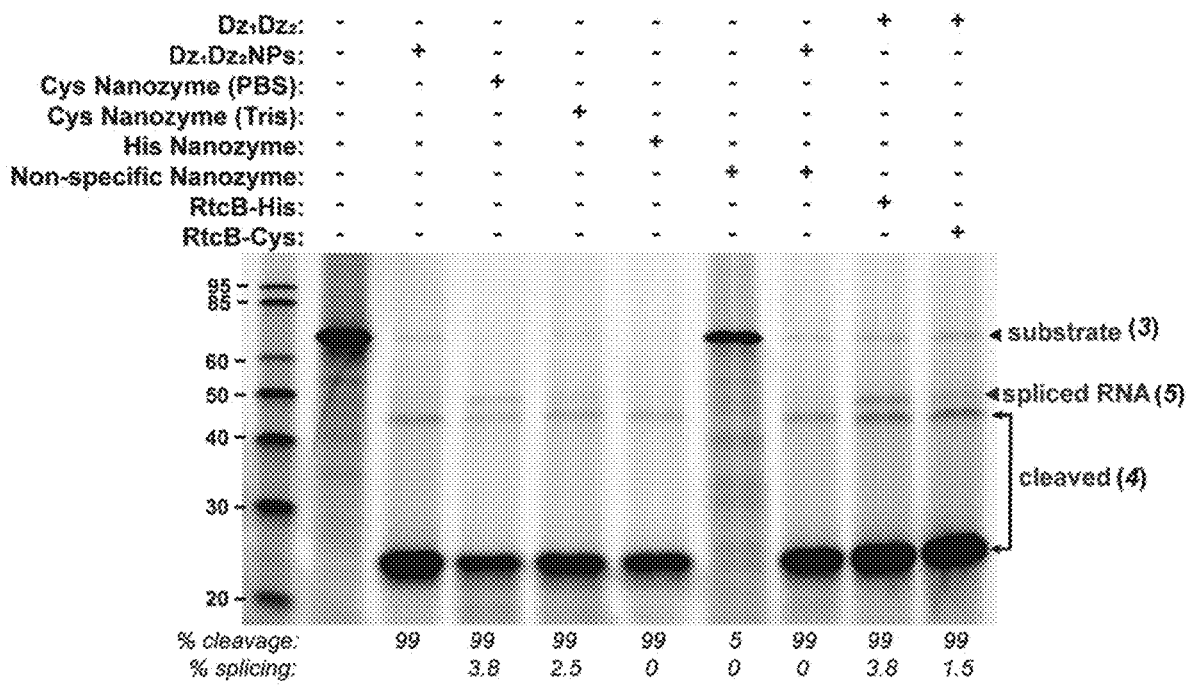
FIG. 6F is a gel showing the role of buffer and immobilization chemistry in tuning nanozyme efficiency. Lane 2: DNA/RNA hybrid substrate 3 alone; lane 3, negative control with $Dz_1Dz_2NPs$ without RtcB; lane 4, nanozyme, produced by RtcB incubated in 1× PBS; lane 5, nanozyme produced by RtcB incubated in 100 mM Tris; lane 6, nanozymes produced by incubation with RtcB-His; lane 7, inactive nanozyme, produced with non-specific DzNPs incubated with RtcB-Cys in 100 mM Tris; lane 8, inactive nanozyme supplemented with active $Dz_1Dz_2NP$; lane 9, soluble 37.5 nM RtcB-His in presence of excess $Dz_1/Dz_2$; lane 10, soluble 37.5 nM RtcB-Cys in presence of excess $Dz_1/Dz_2$. Nanozyme concentration was 25 nM in all lanes. Arrow indicates splice.
Figure 7:
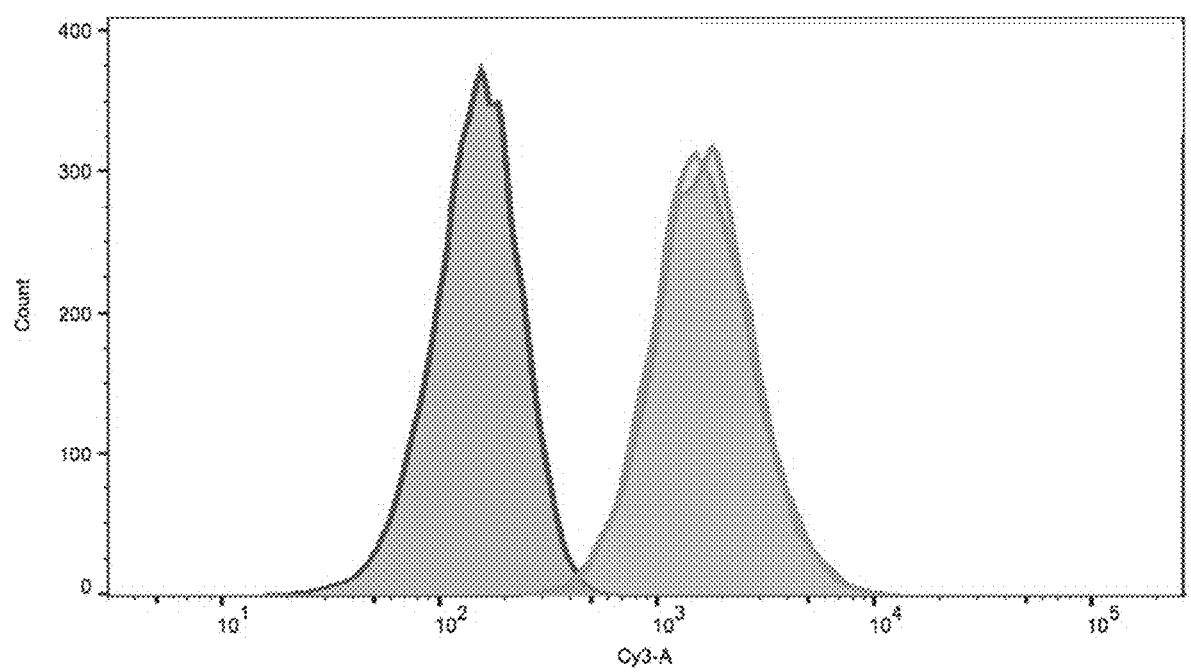
FIG. 7 shows flow cytometry data of $Dz_1Dz_2NPs$ and nanozymes entering MDA-MB-231 cells. Dark indicates non-fluorescent control cells without exposure to nanoparticles. Grey indicates MDA-MB-231 cells exposed to 5.6 nM Cy3b-labeled $Dz_1Dz_2NPs$ for 24 h. Light indicates cells exposed to 6.2 nM Cy3b-labeled nanozymes for 24 h. Both sets of Cy3b-labeled NPs suggest uptake, as indicated by a shift to the right as compared to control non-fluorescent cells. Therefore, RtcB does not appear to inhibit nanozyme uptake into this cell line.

Despite the low copy number of RtcB molecules per nanozyme, the activity of the nanozyme was tested in splicing an RNA substrate. Soluble DNAzymes with and without RtcB enzyme were used as positive and negative controls, respectively. After overnight, RtcB-Cys incubation, the fresh nanozymes were washed three times with 100 mM Tris-HCl buffer to remove excess soluble RtcBCys. After each wash, nanozyme aliquots were then mixed with substrate 3 and incubated at 37° C. for 2 h. Nanozymes digested the RNA target and showed a splicing efficiency of 3% after the third wash at 24 nM concentration of nanozyme. Another set of experiments was conducted, concentrating the nanozymes in each reaction up to ~200 nM. In this case, nanozyme splicing reactions were performed in triplicate, and splice product was as high as 10% (FIG. 6E), as determined by band intensities. Increasing the amount of nanozymes did increase the amount of splice product within the range of nanozyme concentrations tested, although the increase was not linear, due, in part, to decreasing activity of RtcB-Cys as it ages. Further experiments were then conducted with additional controls, such as creation of a nanozyme with RtcB-Cys and nonspecific DNAzymes. This construct was unable to cleave or splice target RNA (FIG. 6F, lane 7). RtcB-Cys should be located on the same particle as the target-specific DNAzymes to effect splicing. Nonspecific nanozymes that included RtcB-Cys were unable to splice the target even after active $Dz_1Dz_2NPs$ were introduced (FIG. 6F, lane 8).

Nanozyme splicing reaction is most optimal when the nuclease and ligase activity are localized to the same particle. An additional set of experiments were performed where the activity of the complete nanozyme was compared against that of a binary mixture of particles where the nuclease and ligase activities are isolated onto different particles. Taken together, the lower yield when using binary mixtures of particles is likely due to the substrate associating with the $Dz_1Dz_2NPs$ and thus reducing the association with the RtcB. Finally, splice reactions were tested with excess DNAzymes and soluble RtcB equivalent to the amount of RtcB on nanozymes. Splicing was found to be equivalent to nanozyme splicing (FIG. 6F, lanes 9-10) indicating that RtcB activity is maintained on the AuNP surface. These experiments indicate that E. coli RtcB is likely a single turnover enzyme and, thus, the limiting reagent in the splice reaction. Overall, this nanozyme shows utility in splicing RNA step—loops. For cellular splicing, it is possible that RtcB does not need to be included on the nanozyme, since endogenous RtcB is already expressed and may be recruited to the particle for splicing.

RtcB and DNAzymes, natural and synthetic enzymes, respectively, can be coupled to a gold nanoparticle and work together to splice RNA targets with up to a 10% yield. This activity is observed despite direct coupling of the RtcB to the gold nanoparticle surface. This nanozyme is the first example of a splicing nanoparticle system and the only known combination of a natural and synthetic enzyme for splicing. RtcB and DNAzymes are on the same particle to achieve splicing and generally do not complement each other on separate particles. The cysteine residues on RtcB are important for RtcB binding to the $Dz_1Dz_2NPs$, without which, no nanozyme is formed; and after washing of $Dz_1Dz_2RtcB$-HisNPs, no detectable splicing is observed. Additionally, DNAzymes and RtcB also splice RNA targets up to 45-66% yield when including excess RtcB in solution. This system provides a completely new method of RNA splicing that adds to the toolkit for in vitro work. Since DNAzyme—NP conjugates and nanozymes readily enter cells in vitro and DNAzyme—NP conjugates have shown uptake in vivo, (Somasuntharam, et al. 2016, Biomaterials 83, 12-22) it also provides a platform with which to conduct cellular splicing.

Expression and Purification of Cysteine-Modified RtcB

RtcB that had been modified with two cysteine residues before the N-terminal His-tag was expressed under a lac-I inducible promoter (pQE70™) and transformed into E. coli BL21. Five mL of LB (100 µg/mL Amp) was inoculated with a single colony of the above transformant and grown at 37° C. overnight. This culture was then used to inoculate 250 mL of LB (100 µg/mL Amp), which was grown at 37° C. shaking until OD600=0.6. Expression was then induced by addition of 0.1 mM IPTG, and the culture was grown for 4 h at 37° C. The culture was spun down at 4000 rpm at 6° C. for 20 min, and the pellet was kept on ice. Cell pellets were resuspended in a total of 10 mL of lysis buffer [50 mM sodium phosphate, 300 mM NaCl, 10 mM imidazole], supplemented with 100 µL of Protease Inhibitor Cocktail (PIC™), 60 µL of lysozyme [20 mg mL—1 stock], and 5-10 µL of benzonase. The resuspended cells were incubated on ice for 20 min, then sonicated for 3.5 min: 15 s pulse, 15 s rest. The lysate was then centrifuged at 4° C., 4000 rpm for 30 min. Ni-NTA beads (QIAGEN™, cat. no. 30210) were prepared by adding 1.2 mL of the resin slurry into a 15 mL Falcon tube. Slurry was centrifuged at 4000 rpm for 2 min, the ethanol was decanted, and the beads were resuspended in 4 mL of lysis buffer. The tube was shaken for 2 min, centrifuged for 2 min, and decanted and rinsed with lysis buffer two more times. The cell lysate was added to the Ni-NTA beads, and the beads were resuspended and rotated on a nutating mixer at 4° C. for 0.5-1.5 h. The beads were then transferred to a 30 mL propylene column, and the initial flow through was collected. The column was washed, with the elutions collected, as follows: 20 mL wash 1, 50 mM potassium phosphate (pH 7.8), 150 mM NaCl, 10 mM imidazole; 15 mL wash 2, 50 mM potassium phosphate (pH 7.8), 150 mM NaCl, 50 rnM imidazole; 1 mL elution 1, 50 mM potassium phosphate (pH 7.8), 150 mM NaCl, 250 mM imidazole; 1 mL elution 2, 50 mM potassium phosphate (pH 7.8), 150 mM NaCl, 500 mM imidazole; 1 mL elution 3, 50 mM potassium phosphate (pH 7.8), 150 mM NaCl, 1000 mM imidazole. A 12% PAGE gel was run for each fraction to determine which fraction contained the majority of the protein. Ten microliters of each fraction was mixed with 10 µL of SDS loading dye and boiled in a thermocycler on the boil cycle for 10 min at 95° C. Fifteen microliters was loaded onto a 12% SDS-PAGE gel and run for 40 min at 220 V, 60 mA. The resulting gel was stained with Coomassie blue 30 min, then destained [40% methanol, 10% glacial acetic acid]. Fractions with protein were dialyzed against 1 L of cold storage buffer (50 mM HEPES/10 mM $MgCl_2$). The concentration of the protein was verified by a NanoDrop™2000c spectrophotometer. Aliquots (50 µL) of RtcB protein were flash frozen in liquid nitrogen and stored in a −80° C. freezer.

DNAzyme Design

Two DNAzymes were adopted from Cairns et al. 1999 Nat. Biotechnol. 17, 480-486; Ruble et al. 2012 Inorg. Chim. Acta 380, 386-391. These were selected because of either relatively rapid catalysis or good activity at low $Mg^{2+}$ concentration. The first DNAzyme ($Dz_1$), DT-99, has 9 nt binding arms and is active against HPV, with a kobs of 0.21 min-1 at 10 mM Mg2+. The sequence is 5'-GTTTCTCTAGGCTAGCTACAACGAGTGTTCTTG-3' (SEQ ID NO: 6), with the catalytic core bold. The second DNAzyme also has 9 nt binding arms and is active against the VEGF receptor at 0.01 mM $Mg^{2+}$. The sequence is 5'-TGCTCTCCAGGCTAGCTACAACGACCTGCACCT-3' (SEQ ID NO: 8).

Designing Construct 3

In order to confirm splicing on another platform, a 5'-FAM-labeled 67 nt synthetic DNA/RNA hybrid was ordered from IDT™ as shown ("r" indicates ribonucleotides): 5'-AGACGAGTCTCACGrCrArArGrArArCrArCr-GrUrArGrArGrArArArCrArGrGrUrGrCrArGr GrGrUrGr-GrArGrArGrCrAGTCGTGAGACTCGTC-3' (SEQ ID NO: 9).

This sequence contained a DNA step—loop and the recognition sites for both the DT-99 (italicized) and VEGFR DNAzymes, allowing the removal of a 19-bp intron. Cleavage sites for each DNAzyme are in bold.

Designing Construct 6

To produce stem-loop RNA 6 (FIG. 1F), a 95 bp stem-loop RNA was designed retaining the stem-loop from tRNA$^{Glu}$, and adding the recognition sites of $Dz_1$ and $Dz_2$ to form a 42 nt single-stranded loop region that can be spliced by the removal of a 20 nt intron segment. The cDNA sequence with an attached 3' T7 promoter (bold) was custom synthesized by Integrated DNA Technologies (IDT) as an Ultramer™ oligo, as follows: 5'-TGGCTCCGATAT-CACGCTTACTGCTCTC-CACCCTGCACCTGGTTTCTCTACGTGTT CTTGCGT-GATATCGGAGCCAGATCAGTCGATACATCAGGTATAGT-GAGTCGTATTA A-3'(SEQ ID NO: 13) (see FIG. 1F, cDNA 6).

To produce stem-loop RNA 6 for in vitro splicing experiments as shown in FIGS. 4A and 4B, the 95 bp RNA was transcribed using the AmpliScribeT7-flash™ kit (Epicentre, Madison, Wis.). After in vitro transcription, the stem-loop RNA was 5'-end labeled with a fluorescein.

Preparation of DNAzyme-Functionalized Gold Nanoparticles ($Dz_1Dz_2NPs$)

To prepare maximally packed $Dz_1Dz_2NPs$, the 3'-thiolated T10-linker DNAzymes were first ordered from Integrated DNA Technologies™ (IDT). Their sequences are as follows:

```
for the DT-99 DNAzyme,
                                        SEQ ID NO: 20)
GTTTCTCTAGGCTAGCTACAACGAGTGTTCTTGTTTTTTTTTT/

3ThioMC3-D/, and for the VEGFR DNAzyme,
                                       (SEQ ID NO: 21)
TGCTCTCCAGGCTAGCTACAACGACCTGCACCTTTTTTTTTTT/

3ThioMC3-D/.
```

Next, 60 nmol of each DNAzyme was reduced in 1 mL of 0.1 M DTT in disulfide cleavage buffer [170 mM phosphate buffer (pH=8.0)] and allowed to incubate at RT for 2 h with occasional vortexing. A Nap-25™ column (GE Healthcare) was flushed with four column volumes of Nanopure™ water. One mL of reduced sample was applied to the column and allowed to flow through completely. Then, 1.5 mL of Nanopure™ water was allowed to enter the column completely. Samples were eluted with 2.5 mL of Nanopure™ water, collecting 4 drops at a time in microcentrifuge tubes. The absorbance of the tubes was quantified on a Nano-Drop™ 2000c spectrophotometer at 260 nm, and fractions with DNAzymes were combined. The volume of the sample was recorded, and DNAzyme concentrations were determined from UV absorbance. To each 1 mL of AuNPs, 2 nmol of each of the reduced DNAzymes was added in a cleaned EPA vial (4 nmol of total DNAzymes). The vial was wrapped in foil and allowed to equilibrate on an orbital shaker overnight at RT. The following day, phosphate adjustment buffer [100 mM phosphate buffer (pH 7.0)] was added to the $Dz_1Dz_2NPs$ to 9 mM final phosphate concentration. SDS was added to ~0.1% (w/v). The tubes were wrapped in foil and incubated on an orbital shaker for 30 min at RT. Afterward, NaCl was added to the $Dz_1Dz_2NPs$ with salting buffer [10 mM phosphate buffer (pH 7.0), 2 M NaCl] in eight increments of final concentration as follows: 0.05, 0.1, 0.2, 0.3, 0.4, 0.5, 0.6, and 0.7 M. After each addition, the $Dz_1Dz_2NPs$ were sonicated in a bath sonicator (VWR 97043-968) 20-30 s, wrapped in foil, and incubated on an orbital shaker 20 min. Salt additions were continued until 0.7 M NaCl was reached. $Dz_1Dz_2NPs$ were stored in 4° C. cold room until use.

DNAzyme-Functionalized Gold Nanoparticle Splicing Assay.

To test whether $Dz_1Dz_2NPs$ plus soluble RtcB were active for splicing, 20 µL reactions were setup with either gold conjugates containing both DNAzymes or single DNAzyme gold particles mixed as follows: 50 mM Tris-HCl (pH 7.4 at 37° C.), 1.5 mM MnC12, 150 mM NaCl, 9.09 nM DNAzyme conjugates (each conjugate), 0.4 µM 5'-FAM labeled step—loop RNA. This reaction was incubated in a water bath at 37° C. for 2 h, after which 2.2 µM RtcB and 0.4 mM GTP were added, and the reaction continued for another 1 h. After incubation, 10 µL samples were quenched in stop solution (5 µL of 95% formamide, 10 mM EDTA, and 5 µL of Ultrapure™ water (Invitrogen)). Samples were subjected to 15% polyacrylamide gel electrophoresis (PAGE) in 1×Tris-borate EDTA (TBE) buffer preheated to 70° C. for 30 min. PAGE gel was imaged on a Typhoon TRIO Variable Mode Imager™ (Amersham Biosciences) at 600 PMT.

Nanozyme Uptake into MDA-MB-231 Cells.

An experiment was performed to determine whether complete nanozymes could enter a model mammalian cell line (MDA-MB-231). Nanozymes and $Dz_1Dz_2NPs$ were synthesized. The thiolated-oligonucleotides were added per 1 ml AuNPs were as follows: 1 nmol of a Cy3b-labeled strand, 1.5 nmol $Dz_1$ and 1.5 nmol $Dz_2$. MDA-MB-231 cells were plated in a 24-well plate 50,000 cells per well in 500 µl of DMEM+10% FBS, 2% L-glutamine and 1% penicillin-streptomycin and grown for 24 h at 37° c., 5% $CO_2$. Afterward, 5.6 nm of washed Cy3b-labeled $Dz_1Dz_2NPs$ and 6.2 nm of Cy3b-labeled nanozyme were added to a total volume of 300 µl media and added to 3 wells and 1 well of MDA-MB-231 cells, respectively (both were washed in 1× PBS. The nanozymes were only washed 1 time, to remove excess RtcB-Cys). The cells were then incubated for 24 h at 37° c., 5% $CO_2$. After the incubation period, the cells were washed with 500 µl 1×PBS and trypsinized (300 µl) for 5 min at 37° c., 5% $CO_2$. Afterward, 700 µl media was added to the wells and the cells were spun down at 300 g for 5 min in a tabletop centrifuge and washed two times with 1 ml 1×PBS. The cells were then transported on ice and 10,000 cells were measured for each sample on a flow cytometer. Triplicate cells without exposure to NPs were measured as a control.

Measurement of RtcB on Nanozyme Conjugates

To 100 µL of 50.5 µM RtcB-Cys in 1×PBS, 0.1 mg of dried Alexa488 was added and allowed to react 2.5 h on ice. The resulting mixture was run through a P4 gel in 1×PBS. The degree of labeling (DOL) was calculated with the equation:

$$DOL = \frac{A_{max} \times MW}{[protein] \times \varepsilon_{dye}}$$

where MW is the molecular weight of the protein, $\varepsilon_{dye}$ is the extinction coefficient of the dye at its absorbance maximum 488 nm, and the protein concentration is in mg mL$^{-1}$.

$Dz_1Dz_2NPs$ (1 mL) were washed as previously described and resuspended in 100 µL of PBS (30 µL of Nanopure water, 70 µL of 1×PBS). To this sample, 13.6 µL of 41.8 µM (DOL=1.4) Alexa488-RtcB-Cys was added and allowed to incubate overnight at 4° C. The $Dz_1Dz_2NP$—Alexa488-RtcB-Cys in 100 mM Tris-HCl (pH 7.43 at 37° C.) was washed three times by first increasing the volume of the sample to 500 µL, spinning down at 13000 rpm in a table top centrifuge, removing the supernatant, and repeating twice more. After the last removal of the supernatant, 40 µL of 100 mM Tris-HCl was added, and the sample absorbance at 520 nm was measured with a NanoDrop™ 2000c spectrophotometer. Next, 5 µL of 5 M potassium cyanide (KCN) was added to a final volume of 52 µL and incubated on ice 45 min. The sample was increased in volume to 100 µL with 100 mM Tris-HCl. Additionally, a standard curve was then created of Alexa488—tcB-Cys in 0, 10, 50, 100, 200, and 400 nM concentrations. The fluorescence emission of Alexa488—RtcB-Cys samples was measured in a Horiba Scientific Dual-FL™ fluorimeter with 10 accumulations. The data was plotted in Excel™, and the emission at 488 nm for each sample was recorded. Using the standard curve, the average number of RtcB on each $Dz_1Dz_2NP$ was calculated.

Calculation of DNAzymes per AuNP

The number of DNAzymes per AuNP was approximated using the Quant-iT OliGreen™ ssDNA Reagent and Kit (ThermoFisher, Grand Island, N.Y.), after releasing the DNAzymes from the gold core. Briefly, 100 µL of DzNPs were aliquoted in 0.2, 0.4, 0.6, and 0.8 nM amounts in TE buffer (10 mM Tris-HCl, 1 mM EDTA, pH 7.5), and the gold core was dissolved with 1 µL of 5 M potassium cyanide (KCN), which was added to each well. A well with TE buffer but no DzNPs served as the control. The AuNP core was allowed to dissolve for 30 min, releasing the DNAzymes. An equal volume (100 µL) of 1×OliGreen™ reagent made up in TE buffer was added to each well and pipetted up and down to mix. The resulting wells were imaged immediately on a Bio-Tek Synergy HT™ plate reader with an approximately 2 min lag time. The fluorescence intensity at 485/528 nm excitation/emission was compared to a standard curve of soluble DNAzymes. This standard curve was produced by diluting a stock of each DNAzyme (4 µg/mL) to known concentrations (0.1, 0.2, 0.5, 0.75, 1, and 2 µg/mL) in 100 µL of TE buffer. After adding 1×OliGreen™ reagent, fluorescence intensities at each concentration were measured and plotted. Using this plot, the fluorescence intensity corresponding to the number of DNAzymes per well could be determined, and this number was divided by the AuNP concentration to approximate the number of DNAzymes per NP.

The invention claimed is:

1. A composition comprising a particle comprising;
   i) a first site-specific RNA cleaving nucleic acid,
   ii) a second site-specific RNA cleaving nucleic acid, and
   iii) a ligating enzyme, wherein the ligating enzyme is RNA cyclase B;
   wherein the first site-specific RNA cleaving nucleic acid comprises a cleaving sequence flanked on a 3' end with a first sequence that hybridizes to a first target sequence and flanked on the 5' end with a second sequence that hybridizes to a second target sequence; and
   wherein the second site specific RNA cleaving nucleic acid comprises a cleaving sequence flanked on the a 3' end with a third sequence that hybridizes to a third target sequence and flanked on the 5' end with a fourth sequence that hybridizes to a fourth target sequence.

2. The composition of claim 1 wherein the particle is a gold nanoparticle.

3. The composition of claim 1 wherein the ligating enzyme comprises a cysteine, dicysteine, or polycysteine flanked on the N-terminal end or C-terminal end.

4. The composition of claim 1 wherein the ligating enzyme comprises (SEQ ID NO: 1)
5'-CCGNYELLTTENAPVKMWTKGVPVEADARQQLINTAKMPFIFKHIAVM

PDVHLGKGSTIGSVIPTKGAIIPAAVGVDIGCGMNALRTALTAEDLPENLA

ELRQAIETAVPHGRTTGRCKRDKGAWENPPVNVDAKWAELEAGYQWLTQKY

PRFLNTNNYKHLGTLGTGNHFIEICLDESDQVWIMLHSGSRGIGNAIGTYF

IDLAQKEMQETLETLPSRDLAYFMEGTEYFDDYLKAVAWAQLFASLNRDAM

MENVVTALQSITQKTVRQPQTLAMEEINCHHNYVQKEQHFGEEIYVTRKGA

VSARAGQYGIIPGSMGAKSFIVRGLGNEESFCSCSHGAGRVMSRTKAKKLF

SVEDQIRATAHVECRKDAEVIDEIPMAYKDIDAVMAAQSDLVEVIYTLRQV

VCVKG.

5. The composition of claim 1 wherein the first and second RNA cleaving nucleic acids are attached to the particle through the 3' end.

6. The composition of claim 1 wherein the first site-specific RNA cleaving nucleic acid comprises GGCTAGCTACAACGA (SEQ ID NO: 2) flanked on the 3' end with the first sequence and the 5' end with the second sequence.

7. The composition of claim 1 wherein the second site-specific RNA cleaving nucleic acid comprises GGCTAGCTACAACGA (SEQ ID NO: 2) flanked on the 3' end with the third sequence and the 5' end with the fourth sequence.

8. The composition of claim 1 wherein the first or second target sequence are not identical to the third or fourth target sequence.

9. A composition comprising a ligating enzyme, wherein the ligating enzyme is RNA cyclase B, and a particle comprising;
   i) a first site-specific RNA cleaving nucleic acid,
   ii) a second site-specific RNA cleaving nucleic acid, and
   wherein the first site-specific RNA cleaving nucleic acid comprises a cleaving sequence flanked on a 3' end with a first sequence that hybridizes to a first target sequence and flanked on the 5' end with a second sequence that hybridizes to a second target sequence; and
   wherein the second site specific RNA cleaving nucleic acid comprising a cleaving sequence flanked on the a 3' end with a third sequence that hybridizes to a third target sequence and flanked on the 5' end with a fourth sequence that hybridizes to a fourth target sequence.

10. The composition of claim 9 wherein the particle is a gold nanoparticle.

11. The composition of claim 9 wherein the ligating enzyme comprises a cysteine, dicysteine, or polycysteine flanked on the N-terminal end or C-terminal end.

12. The composition of claim 9 wherein the ligating enzyme comprises

```
                                                 (SEQ ID NO: 1)
5'-CCGNYELLTTENAPVKMWTKGVPVEADARQQLINTAKMPFIFKHIAVM

PDVHLGKGSTIGSVIPTKGAIIPAAVGVDIGCGMNALRTALTAEDLPENLA

ELRQAIETAVPHGRTTGRCKRDKGAWENPPVNVDAKWAELEAGYQWLTQKY

PRFLNTNNYKHLGTLGTGNHFIEICLDESDQVWIMLHSGSRGIGNAIGTYF

IDLAQKEMQETLETLPSRDLAYFMEGTEYFDDYLKAVAWAQLFASLNRDAM

MENVVTALQSITQKTVRQPQTLAMEEINCHHNYVQKEQHFGEEIYVTRKGA

VSARAGQYGIIPGSMGAKSFIVRGLGNEESFCSCSHGAGRVMSRTKAKKLF

SVEDQIRATAHVECRKDAEVIDEIPMAYKDIDAVMAAQSDLVEVIYTLRQV

VCVKG.
```

13. The composition of claim 9 wherein the first and second RNA cleaving nucleic acids are attached to the particle through the 3' end.

14. The composition of claim 9 wherein the first site-specific RNA cleaving nucleic acid comprises GGCTAGCTACAACGA (SEQ ID NO: 2) flanked on the 3' end with the first sequence and the 5' end with the second sequence.

15. The composition of claim 9 wherein the second site-specific RNA cleaving nucleic acid comprises GGCTAGCTACAACGA (SEQ ID NO: 2) flanked on the 3' end with the third sequence and the 5' end with the fourth sequence.

16. The composition of claim 9 wherein the first or second target sequence are not identical to the third or fourth target sequence.

* * * * *